United States Patent [19]

Eckert et al.

[11] 4,111,933

[45] Sep. 5, 1978

[54] PROTECTION OF FUNCTIONAL GROUPS DURING REACTION AND THEIR SUBSEQUENT RESTORATION

[75] Inventors: Heiner Eckert; Ivar Ugi, both of Munich; Hans-Joachim Kabbe, Leverkusen, all of Fed. Rep. of Germany

[73] Assignee: Bayer Aktiengesellschaft, Leverkusen, Fed. Rep. of Germany

[21] Appl. No.: 792,080

[22] Filed: Apr. 28, 1977

[30] Foreign Application Priority Data

Apr. 30, 1976 [DE] Fed. Rep. of Germany ....... 2619247

[51] Int. Cl.² ............................................. C07D 499/04
[52] U.S. Cl. .......................... 260/239.1; 260/112.5 R; 260/306.7 C; 260/332.2 R; 544/16; 544/17; 544/19; 562/433; 562/452; 562/470; 562/489; 562/507; 562/575; 562/557; 562/563; 562/562; 562/567; 562/440; 562/445; 562/446
[58] Field of Search ...................... 260/239.1, 306.7 C, 260/243 C, 112.5, 514 R, 514 J, 518 R, 519, 534 R, 332.2 R, 515 P; 542/16, 17, 19

[56] References Cited

PUBLICATIONS

Grimshaw, J. Chem. Society (London), pp. 7136–7139 (1965).

*Primary Examiner*—Gerald A. Schwartz
*Attorney, Agent, or Firm*—Burgess, Dinklage & Sprung

[57] ABSTRACT

In the process for preparing an organic compound of the formula

A' — X in which
X is an amino group, a hydroxyl group or a carboxyl group, and
A' is the remainder of the molecule, from an organic compound of the formula

A — X in which
A is the remainder of the molecule which can undergo reaction to form A', by converting A — X into a compound of the formula

A — Z — COOR in which
Z is —NH—, —O— or a direct C—C bond, and
R is a radical of the formula

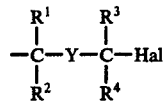

in which
Y is a direct C—C single bond, the —CH=CH— group or an arylene group,
$R^1$ to $R^4$ each independently is hydrogen, halogen or an alkyl, aryl, aralkyl, alkoxycarbonyl, alkylaminocarbonyl, arylaminocarbonyl or cycloalkylaminocarbonyl radical, or
$R^1 + R^2$ and $R^3 + R^4$ each independently completes a 5- or 6-membered carbocyclic ring, or
$R^1$ and $R^3$ conjointly with the grouping —C—Y—C— forms a carbocyclic ring with 5 or 6 carbon atoms, and Hal is halogen, thereby to protect X, then converting A — Z — COOR into a compound of the formula

A' — Z — COOR and then treating the compound A' — Z — COOR to restore the group X, the improvement which comprises effecting the treatment of the compound A' — Z — COOR with an alkali metal compound of a complex of monovalent cobalt. The process is applicable particularly to aminocarboxylic acids including intermediates from various stages of the synthesis of penicillins and cephalosporins.

20 Claims, No Drawings

PROTECTION OF FUNCTIONAL GROUPS DURING REACTION AND THEIR SUBSEQUENT RESTORATION

The present invention relates to a process for protecting functional groups in compounds and in particular for protecting amino groups, hydroxyl groups and/or carboxyl groups.

It is known that in cases where reactions are carried out with compounds which have several reactive groups such reactions proceed in a clear manner and with high yields only when those reactive groups which are not intended to participate in the desired reaction are blocked by so-called protective groups. Essential demands made upon protective groups of this type are that they are inert under the conditions of the reaction to be carried out and can subsequently be split off again in a simple manner. The use of such protective groups is known in the field of the synthesis of peptides and peptide-like compounds, such as the β-lactam antibiotics, in which the selective temporary protection of amino groups, hydroxyl groups or carboxyl groups is an important prerequisite (Houben-Weyl, volume 15/1, Ed. E. Wunsch, G. Thieme-Verlag, Stuttgart 1974, page 46 et seq.).

It has now been found that reactive groups can be protected by converting compounds of the general formula $$A-X \quad (I)$$

in which

X is an amino group, a hydroxyl group or a carboxyl group, and

A is the residual part of the molecule intended for further reaction, into a compound of the general formula $$A - Z - COOR$$

in which

A has the above-mentioned meaning,

Z is —NH—, —O— or a direct C—C bond, and

R is a radical of the general formula $$\begin{matrix} R^1 & & R^3 \\ | & & | \\ -C-Y-C-Hal \\ | & & | \\ R^2 & & R^4 \end{matrix} \quad (III)$$

in which

Y is a direct C—C bond, the —CH—CH— group or arylene, $R^1$ to $R^4$ each independently is hydrogen or an alkyl, aryl, aralkyl, halogen, alkoxycarbonyl, alkylaminocarbonyl, arylaminocarbonyl or cycloalkylaminocarbonyl radical, or $R^1 + R^2$ and $R^3 + R^4$ each independently completes a 5- or 6-membered carbocyclic ring, or $R^1$ and $R^3$ conjointly with the grouping —C—Y—C— forms a carbocyclic ring with 5 or 6 carbon atoms, and Hal is hydrogen, and subsequently, after the reaction on part A of the molecule has taken place, liberating the group to be protected by treating the reaction product with alkali metal compounds of complexes of monovalent cobalt.

Alkyl radicals employed are, in general, those with up to 8 C atoms, $C_1$- to $C_4$-alkyl radicals being preferred and $C_1$ to $C_2$-alkyl radicals being particularly preferred. Examples of individual and conjoint radicals which may be mentioned are: methyl, ethyl, propyl, isopropyl, butyl, tert.-butyl, pentyl, hexyl, heptyl, octyl, cyclopentyl, cyclohexyl, cyclopentenyl and cyclohexenyl.

Examples of aryl radicals which may be mentioned are phenyl and naphthyl, phenyl preferably being employed.

Aralkyl radicals employed are, in general, those with 7 to 10 C atoms and preferably with 7 to 8 C atoms. Examples which may be mentioned are benzyl and phenethyl.

Chlorine, bromine, iodine and fluorine may be mentioned as halogens, chlorine, bromine and iodine preferably being employed and chlorine and bromine particularly preferentially being employed.

Possible alkoxycarbonyl radicals are, in general, those with up to 4 carbon atoms in the alkyl radical and those with 1 to 2 C atoms are preferred. Examples which may be mentioned are methoxycarbonyl and ethoxycarbonyl.

Possible alkylaminocarbonyl radicals are, in general, those with up to 8 C atoms in the alkyl radical and this alkyl radical can be straight-chain or branched. Those alkylaminocarbonyl radicals which have 3 to 6 C atoms in the alkyl part are preferably employed. Examples which may be mentioned are propylaminocarbonyl, butylaminocarbonyl, isobutylaminocarbonyl, tert.-butylaminocarbonyl and hexylaminocarbonyl.

Possible arylaminocarbonyl radicals are, in general, those with 6 to 10 C atoms in the aryl part. An example which may be mentioned is phenylaminocarbonyl.

Possible cycloalkylaminocarbonyl radicals are, in general, those with 5 to 6 C atoms in the cycloalkyl part. Examples which may be mentioned are cyclopentylaminocarbonyl and cyclohexylaminocarbonyl.

In the case where Y = arylene, p-phenylene may be mentioned as an example.

The following radicals may be mentioned as examples of radicals of the general formula III which can be used within the scope of the process according to the invention: β-bromocyclohexyl, β-chloroethyl, β-iodoethyl, β-bromoethyl, β,β-dichloroethyl, β,β-diiodoethyl, β,β-dibromoethyl, β,β,β-trichloroethyl, β,β,β-triiodoethyl, β,β,β-tribromoethyl, β-bromo-β-phenylethyl, β-bromo-α-methoxycarbonylethyl, β-bromopropyl, β-chloropropyl, β,β-dibromopropyl, β,β-dichloropropyl, β,γ-dibromopropyl, α,β-dichloropropyl, β,β,β-trichloro-α,α-dimethylethyl, β,β,β-tribromo-α,α-dimethylethyl, β,β,β-trichloro-tert.-butyl, γ-trichloromethylallyl, γ-tribromomethylallyl, p-trichloromethylbenzyl, p-tribromomethylbenzyl, α-tert.-butylaminocarbonyl-β-chloroethyl, α-tert.-butylaminocarbonyl-β-bromoethyl, α-tert.-butylaminocarbonyl-β,β-dichloroethyl, α-tert.-butylaminocarbonyl-β,β-dibromoethyl, α-tert.-butylaminocarbonyl-β,β,β-trichloroethyl, α-tert.-butylaminocarbonyl-β,β,β-tribromoethyl, α-phenylaminocarbonyl-β-chloroethyl, α-phenylaminocarbonyl-β-bromoethyl, α-phenylaminocarbonyl-β,β-dichloroethyl, α-phenylaminocarbonyl-β,β-dibromoethyl, α-phenylaminocarbonyl-β,β,β-trichloroethyl, α-phenylaminocarbonyl-β,β,β-tribromoethyl, α-cyclohexylaminocarbonyl-β,β-dichloroethyl α-cyclohexylaminocarbonyl-β-bromoethyl, α-cyclohexylaminocarbonyl-β,β-dichloroethyl, α-cyclohexylaminocarbonyl-β,β-dibromoethyl, α-cyclohexylaminocarbonyl-β,β,β-trichloroethyl and α-cyclohexylaminocarbonyl-β,β,β-tribromoethyl.

Of these, those preferably employed are: β-chloroethyl, β-bromoethyl, β,β-dichloroethyl, β,β-dibromoethyl, β,β,β-trichloroethyl, β-bromopropyl, β,β-dibromopropyl, β,β-dichloropropyl, γ-trichloromethylallyl and β,β,β-trichloro-tert.-butyl.

The process according to the invention has the advantage that, after controlled reaction of the protected compound, the protective group can be split off in a simple manner and under particularly gentle conditions.

In principle, all compounds which contain further functional groups, intended for further reaction, in addition to the amino group, hydroxyl group and/or carboxyl group to be protected, or contain only the group to be protected and are subjected to intramolecular conversions are suitable as compounds which can be protected by the process according to the invention. For example, reference may be made to those compounds which are known in the field of the chemistry of aminoacids, peptides and β-lactam antibiotics, such as aminoacids and their derivatives, peptides, penicillins, penicillin S-oxides and cephalosporins, as well as aminopenicillanic acid and its derivatives, aminocephalosporanic acid and its derivatives and aminodeacetoxycephalosporanic acid and its derivatives. Attention may be drawn in particular to the protection of functional groups, such as the amino group, by the process according to the invention in the field of the manufacture of semi-synthetic penicillins and cephalosporins by acylation of 6-aminopenicillanic acid, 7-aminocephalosporanic acid or 7-deacetoxycephalosporanic acid, and phenylglycine, p-hydroxyphenylglycine, phenylmalonic acid, thienylmalonic acid and mandelic acid may be mentioned in particular as compounds to be protected.

It is pointed out that those compounds in which more than one functional group is to be protected can also be employed within the scope of the process according to the invention.

Possible amines which can be employed, as compounds to be protected, within the scope of the process according to the invention are aliphatic, aromatic and heterocyclic amines containing at least one further reactive functional group, such as hydroxyl, carboxyl, alkoxycarbonyl, acyloxy or amide, in addition to the amino group to be protected, it also being possible to employ those amines which possess several different functional groups in addition to the amino group to be protected. Examples which may be mentioned are aminocarboxylic acids and their derivatives, such as salts and esters, peptides, peptide-esters and hydroxyaminocarboxylic acids. Aminocarboxylic acids which can be used are, in particular, all the naturally occurring aminoacids. Examples which may be mentioned are: glycine, alanine, valine, leucine, isoleucine, serine, threonine, cystine, methionine, phenylalanine, tyrosine, tryptophane, dioxyphenylalanine, proline, oxyproline, aspartic acid, glutamic acid, glutamine, arginine, lysine, ornithine, histidine and cysteine.

In addition, all the aminocarboxylic acids which are known in the field of the manufacture of semi-synthetic penicillins or cephalosporins by the acylation of 6-APA, 7-ACA or 7-ADCA can also be used. Examples which may be mentioned are phenylglycine, p-hydroxyphenylglycine and 1-aminocyclohexanecarboxylic acid.

In the case of the protection of the amino group in phenylglycine and in p-hydroxyphenylglycine, possible radicals R are, in particular, those such as bromoethyl, chloroethyl, dibromoethyl, dichloroethyl, trichloroethyl, tribromoethyl and β,β-dibromopropyl.

The following may be mentioned as examples of compounds which are obtainable as intermediates and in which the amino group is protected: N-β-bromoethoxycarbonyl-phenylglycine, N-β,β,β-trichloroethoxycarbonyl-phenylglycine, N-β,β-dibromopropoxycarbonyl-phenylglycine, N-β,β-dichloroethoxycarbonylphenylglycine, N,O-bis-β-bromoethoxycarbonyl-p-hydroxyphenylglycine, N,O-bis-β,β,β-trichloroethoxycarbonyl-p-hydroxyphenylglycine, N,O-bis-β,β-dibromopropoxycarbonyl-p-hydroxyphenylglycine, N,O-bis-β,β-dichloroethoxycarbonyl-p-hydroxyphenylglycine, 1-β-bromoethoxy-carbonylaminocyclohexanecarboxylic acid, β,β,β-trichloroethoxycarbonylaminocyclohexanecarboxylic acid, β,β-dibromopropoxycarbonylaminocyclohexanecarboxylic acid and β,β-dichloroethoxycarbonyl-aminocyclohexanecarboxylic acid.

All the aliphatic and aromatic alcohols, as well as the phenols, are possible as compounds in which the hydroxyl group can be protected by the process according to the invention. Examples which may be mentioned are the hydroxyamines and hydroxycarboxylic acids, as well as the hydroxy-acylaminocarboxylic acids and N-acylated p-hydroxyphenylglycine, serine, threonine and thyroxine.

All the aliphatic, aromatic and heterocyclic carboxylic acids which carry at least one further reactive functional group, such as, in general, an amino, hydroxyl, acylamino, acyloxy, alkoxycarbonyl or aminocarbonyl group, are possible as compounds in which the carboxyl group can be protected by the process according to the invention. Examples which may be mentioned are aminocarboxylic acids, N-acylaminocarboxylic acids, hydroxycarboxylic acids, hydroxyaminocarboxylic acids, acyloxycarboxylic acids and dicarboxylic acid monoesters, as well as peptides and N-acylated peptides. The penicillins, penicillin S-oxides, cephalosporins and deacetoxycephalosporins may also be mentioned. The penicillin S-oxides are preferably employed and in this case the following radicals are then preferably employed for R: β-bromoethyl, β,β-dibromoethyl, β,β-dichloroethyl, β,β,β-trichloroethyl, β,β-dibromopropyl, α-tert.-butylaminocarbonyl-β-chloroethyl, α-cyclohexylaminocarbonyl-β-bromoethyl, α-cyclohexylaminocarbonyl-β-chloroethyl, α-cyclohexylaminocarbonyl-β,β-dichloroethyl, α-tert.-butylaminocarbonyl-β,β-dichloroethyl and α-tert.-butylaminocarbonyl-β,β,β-trichloroethyl.

The following may be mentioned as examples of the penicillin S-oxides which are then obtained as intermediates: penicillin-G S-oxide β-bromoethyl ester, penicillin-G S-oxide β-chloroethyl ester, penicillin-G S-oxide β,β-dibromoethyl ester, penicillin-G S-oxide β,β-dichloroethyl ester, penicillin-G S-oxide β,β,β-trichloroethyl ester, penicillin G S-oxide β,β,β-tribromoethyl ester, penicillin-G S-oxide β-bromo-α-tert.-butylaminocarbonylethyl ester, penicillin-G S-oxide β-chloro-α-tert.-butylaminocarbonylethyl ester, penicillin-G S-oxide dichloro-α-tert.-butylaminocarbonylethyl ester, penicillin-G S-oxide β,β,β-trichloro-α-tert.-butylaminocarbonylethyl ester, penicillin-V S-oxide β-bromoethyl ester, penicillin-V S-oxide β-chloroethyl ester, penicillin-V S-oxide β,β-dibromoethyl ester, penicillin-V S-oxide β,β-dichloroethyl ester, penicillin-V S-oxide β,β,β-trichloroethyl ester, penicillin-V S-oxide β,β,β-tribromoethyl ester, penicillin-V S-oxide β-bromo-α-tert.-butylaminocarbonylethyl ester, penicillin-V S-oxide β-chloro-αtert.-butylaminocarbonylethyl ester, penicillin-V S-oxide β,β-dichloro-α-tert.-butylaminocarbonylethyl ester and penicillin-V S-oxide β,β,β-trichloro-α-tert.-butylaminocarbonylethyl ester.

The conversion of amino or hydroxyl groups into the protected form by the process according to the invention is effected by reacting the compound carrying this amino or hydroxyl group with halogenoformic acid esters of the general formula Hal—CO—OR in which Hal and R have the abovementioned meanings.

The reaction of halogenoformic acid esters with amino or hydroxyl groups is in itself known and therefore does not need to be explained in more detail here. The preparation of the halogenoformic acid esters used according to the invention is also carried out by methods which are in themselves known, for example by reacting alcohols R-OH, in which R has the above meaning, with phosgene (in this context see Wagner and Zook. Synthetic Organic Chemistry, Wiley, New York, 1953, page 483).

Examples which may be mentioned of halogenoformic acid esters which can be used are: β-chloroethoxycarbonyl chloride, β-bromoethoxycarbonyl chloride, β-iodoethoxycarbonyl chloride, β-chloroethoxycarbonyl bromide, β-bromoethoxycarbonyl bromide, β,β-dichloroethoxycarbonyl chloride, β,β-dibromoethoxycarbonyl chloride, β,β-dichloroethoxycarbonyl bromide, β,β-dibromoethoxycarbonyl bromide, β,β,β-trichloroethoxycarbonyl chloride, β,β,β-tribromoethoxycarbonyl chloride, β,β,β-trichloroethoxycarbonyl bromide, β-bromo-β-phenylethoxycarbonyl chloride, β-bromo-α-methoxycarbonylethoxycarbonyl chloride, β-bromopropoxycarbonyl chloride, β,β-dibromopropoxycarbonyl chloride, β,β-dichloropropoxycarbonyl chloride, β,γ-dibromopropoxycarbonyl chloride, β,γ-dichloropropoxycarbonyl chloride, β,β,β-trichloro-α,α-dimethylethoxycarbonyl chloride, γ-trichloromethylallyloxycarbonyl chloride, p-trichloromethylbenzyloxycarbonyl bromide, p-tribromomethylbenzyloxycarbonyl chloride and β-bromocyclohexyloxycarbonyl chloride.

Of these, those preferably employed are: β-chloroethoxycarbonyl chloride, β-bromoethoxycarbonyl chloride, β-bromoethoxycarbonyl bromide, β,β,β-trichloroethoxycarbonyl chloride, β,β,β-trichloroethoxycarbonyl bromide, β-bromopropoxycarbonyl chloride, β,β-dibromopropoxycarbonyl chloride, β,γ-dichloropropoxycarbonyl chloride, γ-trichloromethylallyloxycarbonyl chloride and p-trichloromethylbenzyloxycarbonyl bromide.

Amongst these, those particularly preferred are: β-chloroethoxycarbonyl chloride, β-bromoethoxycarbonyl chloride, β,β-dichloroethoxycarbonyl chloride, β,β-dibromoethoxycarbonyl chloride, β,β,β-trichloroethoxycarbonyl chloride, β-bromopropoxycarbonyl chloride, β,β-dibromopropoxycarbonyl chloride, β,β-dichloropropoxycarbonyl chloride and γ-trichloromethylallyloxycarbonyl chloride.

The conversion of the carboxyl group into the protected form by the process according to the invention is, in general, effected by reacting the particular carboxylic acid derivatives with an alcohol of the general formula

HO—R in which

R has the abovementioned meaning.

Examples which may be mentioned of alcohols which can be employed are: β-chloroethyl alcohol, β-bromoethyl alcohol, β-iodoethyl alcohol, β,β-dichloroethyl alcohol, β,β-dibromoethyl alcohol, β,β,β-tribromoethyl alcohol, β-bromo-β-diphenylethyl alcohol, β-bromo-α-methoxycarbonylethyl alcohol, β-bromopropyl alcohol, β,β-dibromopropyl alcohol, β,β-dichloropropyl alcohol, β,γ-dibromopropyl alcohol, β,γ-dichloropropyl alcohol, β,β,β-trichloro-α,α-dimethylethyl alcohol, γ-trichloromethylallyl alcohol, p-trichloromethylbenzyl alcohol, p-tribromomethylbenxyl alcohol and β,β,β-trichloroethanol.

Of these, those preferably employed are: β-chloroethyl alcohol, β-bromoethyl alcohol, β,β,β-trichloroethyl alcohol, β,γ-dichloropropyl alcohol, γ-trichloromethylallyl alcohol and p-trichloromethylbenzyl alcohol.

Amongst these, those particularly preferred are: β-chloroethyl alcohol, β-bromoethyl alcohol, β,β-dichloroethyl alcohol, β,β,β-trichloroethyl alcohol, β,β-dibromopropyl alcohol and γ-trichloromethylallyl alcohol.

In the case of the salts of organic carboxylic acids, it is also possible to convert the carboxyl group into the protected form by reacting such salts with compounds of the general formula Hal—R in which Hal and R have the abovementioned meanings.

Examples which may be mentioned of compounds of the general formula Hal-R are: 1,1,1,2-tetrachloroethane, 1,1,1,2-tetrabromoethane, 1,2-dibromoethane, 1,2-dichloroethane, 1,1,2-tribromoethane, 1,1,2-trichloroethane, 1,2-dibromopropane, 1,2,2-trichloropropane, 1,2,2-tribromopropane, p-bis-chloromethylbenzene, p-trichloromethylbenzyl chloride, 1,4-dibromobut-2-ene, 1,4-dichloro-but-2-ene,α,β-dibromopropionic acid methyl ester, α,β-dichloropropionic acid ethyl ester, α,β-dibromopropionic acid dimethylamide, α,α,β-trichloropropionic acid ethyl ester, α,α,β-trichloropropionic acid methyl ester and α,α,β-trichloropropionic acid dimethylamide.

Of these, those preferably employed are: 1,2-dichloroethane, 1,2-dibromopropane, p-bis-chloromethylbenzene, α,β-dibromopropionic acid methyl ester, α,β-dibromopropionic acid dimethylamide, 1,1,1,2-tetrachloroethane, 1,2-dibromoethane, p-trichloromethylbenzyl chloride, 1,4-dibromo-but-2-ene and 1,4-dichlorobut-2-ene.

Those particularly preferred are: 1,1,1,2-tetrachloroethane, 1,2-dibromoethane, p-trichloromethylbenzyl chloride, 1,4-dibromo-but-2-ene and 1,4dichloro-but-2-ene.

Carboxyl groups can also be converted into the protective groups according to the invention by reacting compounds containing carboxyl groups with carbonyl compounds of the general formula $R^5$—CO—$R^6$ and isonitriles of the general formula $R^7$—NC to give compounds of the general formula

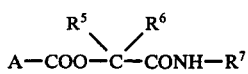

in which
A has the abovementioned meaning
$R^5$ is hydrogen or an alkyl radical, and
$R^6$ is a radical of the general formula

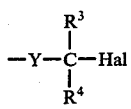

in which
$R^3$, $R^4$, Y and Hal have the abovementioned meanings.

In these formulae, $R^5$ generally represents a straight-chain or branched alkyl radical with up to 8 C atoms, $C_1$-$C_4$-alkyl radicals being preferred and $C_1$-$C_2$-alkyl radicals being particularly preferred. Examples which may be mentioned are: methyl, ethyl, propyl, isopropyl, butyl, isobutyl, tert.-butyl, pentyl, hexyl, heptyl and octyl.

$R^7$ generally represents alkyl which is straight-chain or branched and has 3 to 8 C atoms, phenyl and cycloalkyl with 5 or 6 C atoms in the ring.

The preparation of the carbonyl compounds $R_5$—CO—$R_6$ is in itself known and is described, for example, in Houben-Weyl, volume 7/1 and 7/2a, Verlag Thieme, Stuttgart. The preparation of the isonitriles $R_7$-NC is also carried out in a manner which is in itself known and is described, for example, in Ugi, Isonitriles, Academic Press, New York 1971, page 9.

The protective group according to the invention is split off by treating the protected compound with alkali metal compounds of complexes of monovalent cobalt. In general, the complex compounds of monovalent cobalt which are employed are those which possess the general formula

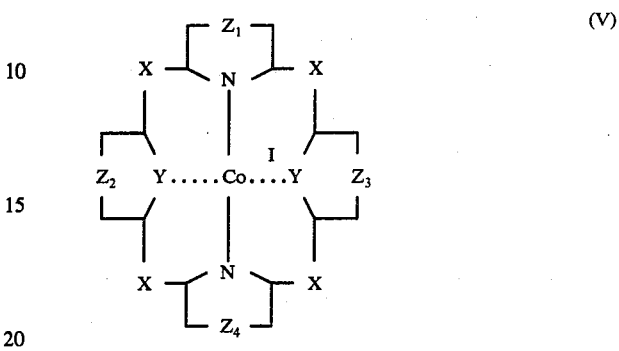

(V)

in which
Y is a hetero-atom, such as nitrogen, oxygen or sulphur,
$Z_1$, $Z_2$, $Z_3$ and $Z_4$ each independently is the grouping CH—CH, N—N or CH—N, which, together with Y or N, form a five-membered ring which is optionally substituted and/or fused to a benzene nucleus, which, in turn, can be substituted, and
X is a nitrogen atom or the grouping —$CR_8$, in which $R_8$ is hydrogen, alkyl preferably of up to 4 C atoms or aryl such as phenyl,
and wherein
the quadridentate ligand, around the cobalt atom, forms an "inner-heterocyclic structure" with 16 ring members and a continuous delocalized $\pi$-electron system.

The cobalt complexes which are derived from the following basic structures:

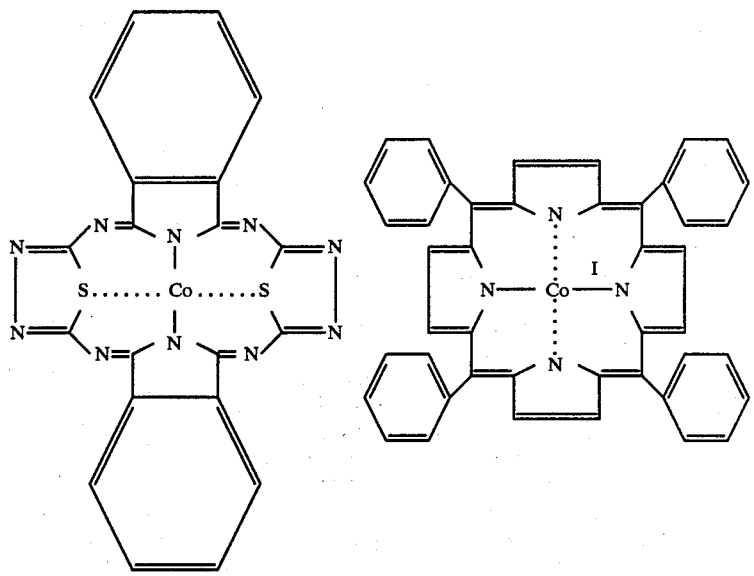

-continued

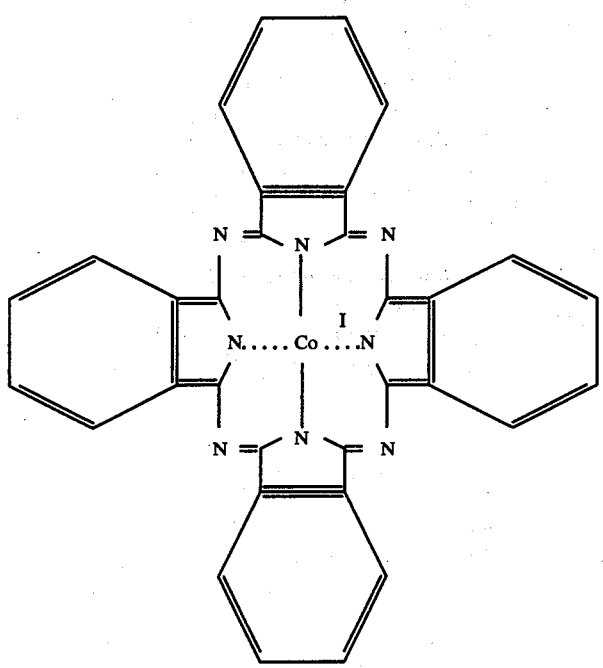

may be mentioned as examples.

Examples which may be mentioned of individual compounds which can be employed within the scope of the process according to the invention are: lithium cobalt-(I)-phthalocyanine, sodium cobalt-(I)-phthalocyanine, potassium cobalt-(I)-phthalocyanine, sodium cobalt-(I)-meso-tetraphenylporphyrine and sodium bis[2-(1'-imino-3'-isoindolenine)-5-amino-1,3,4-thiadiazolatol]-cobaltate-(I).

The cobalt complex compounds listed above are in themselves known and are described, for example, in R. Taube, M. Zach, K. A. Stauske and S. Heidrich, Z, Chem. 3, 392 (1963), H. W. Whitlock and B.K. Bower, Tetrahedron Lett. 1965, 4,827; N.A. Kolesnikov and V. F. Borodkin, Izv. Vyssh. Ucheb Zaved, Khim, Tekhnol. 1972, 880 and P. Day et al., J. Chem. Soc. (A) 1968, 90. The following complex compounds are particularly preferentially employed: lithium cobalt-(I)-phthalocyanine, sodium cobalt-(I)-phthalocyanine and sodium bis-[2-(1'-imino-3'-isoindolenine)-5-amino-1,3,4-thiadiazolato]-cobaltate-(I).

In general, the protective groups are split off at temperatures of about −30 to +50° C and preferably about 0° to 30° C and the molar ratio of protected grouping to alkali metal compound in the particular cobalt-(I) complex in general has a value of about 1:4 to 1:2 and preferably of about 1:3 to 1:2.

In a separate embodiment, the protective group is split off with the aid of alkali metal compounds of monovalent cobalt in the presence of reducing agents, such as, for example, sodium borohydride, sodium amalgam, lithium/benzophenone complexes or sodium/ or potassium/naphthalene adducts. In such cases the reaction can be carried out with smaller amounts of the cobalt complex compounds than indicated above.

The removal of the protective group is generally carried out in the presence of a diluent and diluents which can be used are those compounds which are inert under the reaction conditions. These are aliphatic and aromatic hydrocarbons, such as benzene, toluene, xylene, cyclohexane and methylcyclohexane.

Furthermore, open-chain and cyclic ethers, such as dibutyl ether, tetrahydrofuran, dioxane and ethylene glycol dimethyl ether; ketones, such as acetone, methyl isopropyl ketone, methyl isobutyl ketone and cyclohexanone; esters, such as ethyl acetate or isoamyl acetate; nitriles, such as acetonitrile or propionitrile; amides, such as dimethylformamide, dimethylacetamide, N-methylpyrrolidone and hexamethylphosphoric acid trisamide; tetraalkylureas, such as tetramethylurea and N,N-dimethyl-N',N'-tetramethyleneurea; sulphoxides, such as dimethylsulphoxide, and sulphones, such as tetramethylenesulphone, and also phenols, such as 2,6-di-tert.-butylphenol or 4-chlorophenol, can be employed as diluents. Furthermore, mixtures of the above-mentioned solvents of any desired type can also be used as diluents.

The elimination can also optionally be carried out in the presence of phenols, such as phenol, 2,6-di-tert.-butylphenol or 4-chlorophenol, and the molar ratio of these phenols to the cobalt complexes is from about 4:1 to 1:1, and preferably about 2:1.

Illustrative Examples:

EXAMPLE 1

158 g (2.0 mols) of pyridine in 100 ml of $CH_2Cl_2$ are added dropwise, at −20° to −5° C, to 250 g (2.0 mols) of 2-bromoethanol and 140 ml (2.1 mols) of condensed phosgene in 800 ml of $CH_2Cl_2$ and the mixture is stirred for 1 hour at 20°. It is washed with ice water, ice-cold 10% strength sulphuric acid and ice water and dried over $Na_2SO_4$ and the $CH_2Cl_2$ is stripped off. Vacuum distillation gives 310 g (83%) of 2-bromoethoxycarbonyl chloride. Boiling point$_{10}$ = 60° C.

EXAMPLE 2

79 g (1.0 mol) of pyridine in 50 ml of $CH_2Cl_2$ are added, at −20° to −5° C, to 80.5 g (1.0 mol) of 2-chloroethanol and 70 ml (1.05 mols) of condensed phosgene in 400 ml of $CH_2Cl_2$ and the mixture is stirred for a further 1 hour at 20° C. It is washed with ice water, ice-cold 10% strength sulphuric acid and ice water and dried ($Na_2SO_4$) and the solvent is stripped off. Vacuum distillation gives 123 g (86%) of 2-chloroethoxycarbonyl chloride. Boiling point$_{10}$ = 47° C.

EXAMPLE 3

79 g (1.0 mol) of pyridine in 50 ml of $CH_2Cl_2$ are added, at −20° to −5° C, to 149 g (1.0 mol) of 2,2,2-trichloroethanol and 70 ml (1.05 mols) of condensed phosgene in 400 ml of $CH_2Cl_2$ and the mixture is stirred for a further 1 hour at 20° C. It is washed at 0° C with water, 10% strength sulphuric acid and water and dried ($Na_2SO_4$) and the solvent is stripped off. After vacuum distillation, 177 g (85%) of 2,2,2-trichloroethoxycarbonyl chloride are obtained. Boiling point$_{10}$ = 65°–67° C.

EXAMPLE 4a 174 g (3.0 mols) of propionaldehyde in 300 ml of $CH_2Cl_2$ are added dropwise in the course of 4 hours, at 10 to 15° C, to a solution of 960 g (306 ml, 6.0 mols) of $Br_2$, 1 ml of hydrogen bromide in glacial acetic acid and 300 ml of $CH_2Cl_2$. The solution is stirred at 20° C for 16 hours and the solvent is stripped off at 0° C. The residue is taken up in $CH_2Cl_2$ and the solution is washed with $NaHCO_3$ solution, to which a little $Na_2S_2O_3$ has been added (in order to destroy bromine), and water and dried ($Na_2SO_4$) and the solvent is stripped off at 0° C. The first fraction from vacuum distillation of the oil gives 235 g (36%) of colorless 2,2-dibromopropionaldehyde. Boiling point$_{10}$: 24°–26° C.

EXAMPLE 4b 15 g (0.4 mol) of sodium borohydride are initially introduced into 100 ml of tetrahydrofuran, to which a few drops of triethylamine have been added, and, while stirring vigorously, 43.2 g (0.2 mol) of 2,2-dibromopropionaldehyde in 20 ml of tetrahydrofuran are added dropwise to this mixture. The addition of 10 ml of acetone and the careful addition, while cooling with methanol/solid carbon dioxide, of 100 ml of 5% strength sulphuric acid (evolution of gas) then follows. The reaction mixture is filtered, the filtrate is extracted with a large amount of $CH_2Cl_2$, the extracts are washed with saturated $NaHCO_3$ solution and dried ($Na_2SO_4$) and the solvent is stripped off (43 g of crude product, 99%). Vacuum distillation gives 34 g (78%) of pure 2,2-dibromopropanol. Boiling point$_{10}$ = 64°–66° C. Melting point = 27°–28° C.

EXAMPLE 4c 16 ml (0.22 mol) of liquid phosgene are condensed into 33 g (0.15 mol) of 2,2-dibromopropanol in 150 ml of $CH_2Cl_2$, at −20° C, and 12 ml (0.15 mol) of pyridine in 15 ml of $CH_2Cl_2$ are then added slowly dropwise at −20° C to −5° C and the mixture is stirred for a further 2 hours at 20° C. The solution is washed, at 0° C, with water, 5% strength sulphuric acid and $H_2O$ and dried ($Na_2SO_4$) and the solvent is stripped off (46.1 g of crude product). Vacuum distillation gives 36.3 g (86%) of 2,2-dibromopropoxycarbonyl chloride as a colorless liquid. Boiling point$_{12}$ = 81°–86° C.

EXAMPLE 5

8.9 g (0.1 mol) of L-alanine and 12 g (0.11 mol) of sodium carbonate are dissolved in 50 ml of water and the solution is emulsified with 20.7 g (0.11 mol) of 2-bromoethoxycarbonyl chloride in 50 ml of ether at 15° to 20° C. After about 4 hours (no further $CO_2$), the phases are separated and the aqueous phase is washed with ether, acidified with 2 N sulphuric acid and extracted with $CH_2Cl_2$, the $CH_2Cl_2$ extracts are dried with $Na_2SO_4$ and the solvent is stripped off. Treatment under a high vacuum gives 17 g (71%) of a white wax consisting of 2-bromoethoxycarbonyl-L-alanine. $[\alpha]_D^{25}$ = −20.0 0° ($c$ = 2 in ethanol)

EXAMPLE 6a 3.4 g (42 mmols) of pyridine in 5 ml of $CH_2Cl_2$ are added dropwise, at 0° to 5° C, to 2.79 g (20 mmols) of L-alanine methyl ester-hydrochloride and 4 g (21 mmols) of 2-bromoethoxycarbonyl chloride in 40 ml of $CH_2Cl_2$ and the mixture is stirred for a further 30 minutes at 20° C. It is washed with 5% strength citric acid, water and saturated $NaHCO_3$ solution and dried ($Na_2SO_4$) and the solvent is stripped off. After recrystallizing the residue from pentane/ether (5:1), 3.6 g (71%) of white needles of 2-bromoethoxycarbonyl-L-alanine methyl ester are obtained. Melting point = 47°–48° C.

EXAMPLE 6b

HCl gas is passed into a mixture of 10 g of 2-bromoethoxycarbonyl-L-alanine and 120 ml of methanol and the mixture is stirred for 8 hours at the reflux temperature, concentrated to 30 ml and cooled to 0° C. The ester is filtered off and dried: 9.8 g (92%) of 2-bromoethoxycarbonyl-L-alanine methyl ester.

EXAMPLE 7

4.15 g (22 mmols) of 2-bromoethoxycarbonyl chloride in 5 ml of $CH_2Cl_2$ are added dropwise, at 0° to 5° C, to 3.18 g (22 mmols) of L-alanine tert.-butyl ester and 2 g (25 mmols) of pyridine in 50 ml of $CH_2Cl_2$ and the mixture is stirred for a further 30 minutes at 20° C. It is washed with water, 5% strength citric acid, water, saturated $NaHCO_3$ solution and water and dried ($Na_2SO_4$) and the solvent is stripped off. Recrystallization of the residue from pentane/ether (10:1) gives 5.6 g (86%) of colorless needles of 2-bromoethoxycarbonyl-L-alanine tert.-butyl ester. Melting point = 67° C. $[\alpha]_D^{25}$ = −29.9° ($c$ = 2.3 in ethanol).

EXAMPLE 8

2.51 g (20 mmols) of glycine methyl ester-hydrochloride are reacted as under (6a). 1.55 g (32%) of white crystals of 2-bromoethoxycarbonyl-glycine methyl ester are obtained. Melting point = 65°–66° C.

EXAMPLE 9

7.5 g (50 mmols) of D-C-phenylglycine and 16.8 g (0.2 mol) of $NaHCO_3$ in 50 ml of water are emulsified with 14 g (75 mmols) of 2-bromoethoxycarbonyl chloride in 25 ml of ether, at 20° C. After 3 hours (no further $CO_2$), the phases are separated and the aqueous phase is washed with ether, acidified with half-concentrated hydrochloric acid and extracted with $CH_2Cl_2$. The $CH_2Cl_2$ extracts are washed with water and dried ($Na_2SO_4$) and the solvent is stripped off, whereupon 10 g (66%) of 2-bromoethoxycarbonyl-D-C-phenylglycine are obtained as a white solid. Reprecipitating twice from $CH_2Cl_2$ with pentane gives white crystals. Melting point = 109°–112° C. $[\alpha]_D^{25}$ = −104° ($c$ = 1 in ethanol).

EXAMPLE 10

3.35 g (20 mmols) of L-valine methyl ester-hydrochloride are reacted as in Example 6a. 4.6 g (82%) of white needles of 2-bromoethoxycarbonyl-L-valine methyl ester are obtained. Melting point = 79° C. $[\alpha]_D^{25} = -17.9°$ ($c = 1$ in ethanol).

EXAMPLE 11

26.0 g (0.15 mol) of L-valine tert.-butyl ester are reacted as in Example 7. 40.4 g (83%) of colorless crystals of 2-bromoethoxycarbonyl-L-valine tert.-butyl ester are obtained. Melting point = 59° C. $[\alpha]_D^{25} = -16.0°$ ($c = 3.7$ in ethanol).

EXAMPLE 12

4.95 g (24 mmols) of dicyclohexylcarbodiimide are added, at 0° C, to 4.8 g (20 mmols) of 2-bromoethoxycarbonyl-L-alanine and 5.05 g (44 mmols) of N-hydroxysuccinimide in 100 ml of $CH_2Cl_2$. After 1 hour, 4.15 g (24 mmols) of L-valine tert.-butyl ester in 50 ml of $CH_2Cl_2$ are added and the mixture is stirred for a further 4 hours at 20° C. The dicyclohexylurea is filtered off and the filtrate is washed with water, 5% strength citric acid, water, saturated $NaHCO_3$ solution and water and dried ($Na_2SO_4$) and the solvent is stripped off. The residue is taken up in 20 ml of $CH_2Cl_2$, the residual dicyclohexylurea is filtered off and the solvent is stripped off from the filtrate. This gives 7.3 g (92%) of a colorless oil consisting of 2-bromoethoxycarbonyl-L-alaninyl-L-valine tert.-butyl ester, which crystallizes slowly. Melting point = 61°-63° C. $[\alpha]_D^{25} = -40.6°$ ($c = 1.5$ in ethanol).

EXAMPLE 13

4.4 g (11 mmols) of 2-bromoethoxycarbonyl-L-alaninyl-L-valine tert.-butyl ester are dissolved in 20 ml of TFE at 20° C and after 10 minutes the solvent is stripped off. The residue is dissolved in $NaHCO_3$ solution, the solution is filtered and the filtrate is washed with ether. After acidifying with 1 N HCl, the mixture is extracted with a large amount of $CH_2Cl_2$, the extracts are dried ($Na_2SO_4$) and the solvent is stripped off. This gives 3.2 g (86%) of white crystals of 2-bromoethoxycarbonyl-L-alaninyl-L-valine. Melting point = 140°-142° C. $[\alpha]_D^{25} = -18.4°$ ($c = 1$ in ethanol).

EXAMPLE 14

1.36 g (4.0 mmols) of 2-bromoethoxycarbonyl-L-alaninyl-L-valine are reacted with 0.725 g (5.0 mmols) of L-alanine tert.-butyl ester in the manner described in Example 12. After recrystallizing the product from $CH_2Cl_2$/ether (1:3), 1.45 g (78%) of white crystals of 2-bromoethoxycarbonyl-L-alaninyl-L-valinyl-L-alanine tert.-butyl ester are obtained. Melting point = 181° C (decomposition), $[\alpha]_D^{25} = -58.7°$ ($c = 1$ in ethanol).

EXAMPLE 15

52 g (0.3 mol) of L-valine tert.-butyl ester and 43 g (0.3 mol) of 2-chloroethoxycarbonyl chloride are reacted in the manner described in Example 7. This gives 71 g (85%) of white crystals of 2-chloroethoxycarbonyl-L-valine tert.-butyl ester. Melting point = 47° C. $[\alpha]_D^{25} = -18.0°$ ($c = 2$ in ethanol).

EXAMPLE 16

3.46 g (20 mmols) of L-valine tert.-butyl ester and 5.61 g (20 mmols) of 2,2-dibromopropoxycarbonyl chloride are reacted in the manner described in Example 7. Without recrystallizing the residue, 6.9 g (83%) of an analytically pure oil consisting of 2,2-dibromopropoxycarbonyl-L-valine tert.-butyl ester, which crystallizes out at 0° C, are obtained. Melting point = 44°-46° C. $[\alpha]_D^{25} = -15.3°$ ($c = 1.0$ in ethanol).

EXAMPLE 17

7.55 g (50 mmols) of D-C-phenylglycine are dissolved in 100 ml of water and 55 ml of 1 N sodium hydroxide solution, and 50 ml of ether are added. 15 g (71 mmols) of 2,2,2-trichloroethoxycarbonyl chloride in 70 ml of absolute dioxane and, at the same time, 70 ml of 1 N sodium hydroxide solution are added dropwise in the course of one hour, at $-5°$ C, to the mixture, which is stirred well, and the mixture is stirred for a further 1 hour at 0° C. The mixture (pH = 9.2) is washed with a large amount of ether, acidified with half-concentrated hydrochloric acid and extracted with ethyl acetate. The extracts are washed with water and dried ($Na_2SO_4$) and the solvent is stripped off. Reprecipitation of the product from ethyl acetate with hexane gives 11.9 g (73%) of white crystals of 2,2,2-trichloroethoxycarbonyl-D-C-phenylglycine. Melting point = 145° C. $[\alpha]_D^{25} = -109°$ ($c = 1.1$ in ethanol).

EXAMPLE 18

1.7 g (10 mmols) of p-hydroxy-C-phenylglycine are dissolved in 20 ml of water and 22 ml of 1 N sodium hydroxide solution, and 10 ml of ether are added. 6.2 g (22 mmols) of 2,2-dibromopropoxycarbonyl chloride in 12.5 ml of absolute dioxane and, at the same time, 10 ml of 1 N sodium hydroxide solution are added dropwise in the course of 30 minutes, at 0° C, to the mixture, which is stirred well, and the mixture is stirred for a further 4 hours at 20° C. The mixture (pH = 6.5) is washed with a large amount of ether/petroleum ether (1:1), provided with a lower layer of $CH_2Cl_2$ and acidified with half-concentrated hydrochloric acid at 0° C until the pH is 2.0. The aqueous phase is extracted with $CH_2Cl_2$ and the combined $CH_2Cl_2$ extracts are washed with saturated NaCl solution and dried ($Na_2SO_4$) and the solvent is stripped off. Reprecipitation of the product from methanol with water gives 5.0 g (76%) of white crystals of N,O-di-(2,2-dibromopropoxycarbonyl)-D,L-p-hydroxy-C-phenylglycine. Melting point = 109° C (decomposition).

EXAMPLE 19

15.1 g (0.1 mol) of D-C-phenylglycine and 39 g of 2,2-dibromopropoxycarbonyl chloride are reacted in the manner described under Example 17. After reprecipitation of the product from methanol with water, and drying, 35.4 g (90%) of a white solid consisting of 2,2-dibromopropoxycarbonyl-D-phenylglycine are obtained. $[\alpha]_D^{25} = -86.7°$ ($c = 1.0$ in ethanol).

EXAMPLE 20

8.65 g (50 mmols) of L-valine tert.-butyl ester and 10.6 g (50 mmols) of 2,2,2-trichloroethoxycarbonyl chloride are reacted in the manner described in Example 7. Without recrystallization, 15.4 g (95%) of a white solid consisting of 2,2,2-trichloroethoxycarbonyl-L-valine tert.-butyl ester are obtained Melting point = 31° C. $[\alpha]_D^{25} = -20.0°$ ($c = 1$ in ethanol).

EXAMPLE 21

89 g (1 mol) of L-alanine are ground intensively with 207 g (1.2 mols) of 4-toluenesulphonic acid monohydrate and the mixture is boiled in 250 g (2 mols) of 2-bromoethanol and about 1.5 l of benzene under reflux for about 20 hours, while removing the water of reaction from the system by means of $Na_2SO_4$. After stripping off the solvent, a brown oil, which cannot be made to crystallize, is retained. This is taken up in $CH_2Cl_2$, hydrogen chloride is passed into the solution and the product is precipitated with ether saturated with HCl, the mixture is filtered and the material on the filter is rinsed with ether. This gives 110 g (47%) of small white shiny flakes of L-alanine 2-bromoethyl ester-hydrochloride. Melting point = 129° C. $[\alpha]_D^{25} = -1.5°$ ($c = 4.8$ in water).

EXAMPLE 22

10 g (0.1 mol) of triethylamine in 10 ml of ether are added in the course of 30 minutes, at 0° C. to 11.6 g (50 mmols) of L-alanine bromoethyl ester-hydrochloride in 60 ml of an approximately 1 molar ethereal solution of tert.-butoxycarbonyl fluoride and the mixture is stirred at 20° C for a further 30 minutes. It is filtered, the filtrate is washed with 5% strength citric acid, water and saturated $NaHCO_3$ solution and dried ($Na_2SO_4$), and the solvent is stripped off. Recrystallization of the residue from pentane at −20° C gives 12.5 g (84%) of white crystals of tert.-butoxycarbonyl-L-alanine 2-bromoethyl ester. Melting point = 18°-20° C. $[\alpha]_D^{25} = -36.9°$ ($c = 1.3$ in ethanol).

EXAMPLE 23

10.6 g (40 mmols) of tert.-butoxycarbonyl-L-phenylalanine and 9.3 g (40 mmoles) of L-alanine 2-bromoethyl esterhydrochloride are reacted in the manner described in Example 12. After recrystallization of the product from hexane/ethyl acetate (3:1), 15.4 g (87%) of white crystals of tert.-butoxycarbonyl-L-phenylalaninyl-L-alanine 2-bromoethyl ester are obtained. Melting point = 109°-10° C. $[\alpha]_D^{25} = -17.1°$ ($c = 0.8$ in ethanol).

EXAMPLE 24

8.87 g (20 mmols) of tert.-butoxycarbonyl-L-phenylalaninyl-L-alanine 2-bromoethyl ester are dissolved in 20 ml of trifluoroacetic acid and the latter is stripped off and removed by entraining in absolute tetrahydrofuran. Reprecipitation of the product from $CH_2Cl_2$ with pentane gives 8.8 g (96%) of white needles of L-phenylalaninyl-L-alanine 2-bromoethyl ester-hydrotrifluoroacetate. Melting point = 128°-129° C. $[\alpha]_D^{25} = -8.6°$ ($c = 1.8$ in ethanol).

EXAMPLE 25

3.5 g (15.7 mmols) of carbobenzoxy-L-alanine and 6.85 g (15 mmols) of L-phenylalaninyl-L-alanine 2-bromoethyl ester-hydrotrifluoroacetate are reacted in the manner described in Example 12. After recrystallization of the product from hexane/ethyl acetate (3:1), 6.4 g (78%) of white crystals of carbobenzoxy-L-alaninyl-L-phenylalaninyl-L-alanine 2-bromoethyl ester are obtaned. Melting point = 153°-156° C. $[\alpha]_D^{25} = -46.8°$ ($c = 0.5$ in ethanol).

EXAMPLE 26

3.34 g (15 mmols) of carbobenzoxy-L-alanine, 1.9 ml (16.5 mmols) of tert.-butylisonitrile and 2.06 g (15 mmols) of 2-bromopropionaldehyde are reacted in the manner described under Example 30. Tis gives 5.4 g (86%) of This carbobenzoxy-L-alanine 1-tert.-butylaminocarbonyl-2-bromopropyl ester. Recrystallization from $CH_2Cl_2$ with pentane gives white crystals. Melting point = 129°-130° C. $[\alpha]_D^{25} = -36.2°$ ($c = 0.9$ in ethanol).

EXAMPLE 27

3.5 ml of a 45% strength aqueous solution of chloroacetaldehyde in 10 ml of tetrahydrofuran are added in the course of 10 minutes, at 0° C, to 4.46 g (20 mmols) of carbobenzoxy-L-alanine and 2.5 ml (22 mmols) of tert.-butylisonitrile in 20 ml of tetrahydrofuran and the solution is stirred for a further 2 hours at 20° C. The solvent is stripped off, the residue is taken up in $CH_2Cl_2$, the solution is washed with 5% strength citric acid, water and saturated $NaHCO_3$ solution and dried ($Na_2SO_4$) and the solvent is stripped off. This gives 5.8 g (75%) of a colorless resin consisting of carbobenzoxy-L-alanine 1-tert.-butylaminocarbonyl-2-chloroethyl ester, which crystallizes slowly. Melting point = 64° C, $[\alpha]_D^{25} = -15.1°$ ($c = 1.0$ in ethanol).

EXAMPLE 28

9 g (50 mmols) of C-phenylmalonic acid and 3.8 ml (52 mmols) of thionyl chloride are boiled in 50 ml of absolute ether, to which 1 drop of dimethylformamide has been added, for 5 hours under reflux. The solvent is stripped off, the residue is dissolved in 50 ml of absolute ether, 11g (50 mmols) of 2,2-dibromopropanol are added to the solution and the mixture is boiled for 2 hours under reflux. It is washed with water and the organic phase is extracted with $NaHCO_3$ solution until it gives an alkaline reaction. The combined extracts are washed with ether, acidified with half-concentrated hydrochloric acid and extracted with $CH_2Cl_2$. The $CH_2Cl_2$ extracts are washed with water and dried ($Na_2SO_4$) and the solvent is stripped off. Reprecipitating three times from methanol with water gives 9.9 g (52%) of a colorless oil consisting of C-phenylmalonic acid mono-2,2-dibromopropyl ester.

EXAMPLE 29

4.32 g (20 mmols) of 2,2-dibromopropionaldehyde in 10 ml of $CH_2Cl_2$ are added in the course of 10 minutes, at 0° C, to 5.3 g (20 mmols) of tert.-butoxycarbonyl-L-phenylalanine and 2.5 ml (22 mmols) of tert.-butylisonitrile in 20 ml of $CH_2Cl_2$ and the solution is stirred for a further 4 hours at 20° C. It is washed with 5% strength citric acid, water and saturated $NaHCO_3$ solution and dried ($Na_2SO_4$) and the solvent is stripped off. Reprecipitation of the product from methanol with water gives 10.7 g (95%) of white crystals of tert.-butoxycarbonyl-L-phenylalanine 1-tert.-butylaminocarbonyl-2,2-dibromopropyl ester. Melting point = 119°-20° C. $[\alpha]_D^{25} = -18.3°$ ($c = 1.3$ in ethanol).

EXAMPLE 30

1.6 ml (15 mmols) of bromal in 7 ml of $CH_2Cl_2$ are added in the course of 5 minutes, at 0° C, to 3.34 g (15 mmols) of carbobenzoxy-L-alanine and 1.9 ml (16.5 mmols) of tert.-butylisonitrile and the mixture is stirred for a further 3 hours at 20° C. It is washed with 1 N hydrochloric acid, water and saturated NaHCO$_3$ solution and dried and the solvent is stripped off, whereupon 8.4 g (95%) of a solid consisting of carbobenzoxy-L-alanine 1-tert.-butylaminocarbonyl-2,2,2-tribromoethyl ester are obtained. Recrystallization from CH$_2$Cl$_2$ with pentane gives white crystals. Melting point = 157°-8° C. $[\alpha]_D^{25} = -36.4°$ ($c = 1.0$ in ethanol).

EXAMPLE 31

27 g (0.14 mol) of C-phenylmalonic acid and 22.4 g (0.15 mol) of 2,2,2-trichloroethanol are reacted in the manner described in Example 28. Reprecipitating twice from methanol with water gives 12.7 g (29%) of white crystals of C-phenylmalonic acid mono-2,2,2-trichloroethyl ester. Melting point = 80°-2° C.

EXAMPLE 32

10.4 g (50 mmols) of carbobenzoxyglycine, 2 g (50 mmols) of sodium hydroxide, 50 g of 1,4-dichloro-but-2-ene and potassium iodide sufficient to cover the tip of a spatula, in 125 ml of methanol, are stirred for 5 hours at 20° C. The solvent is stripped off, the residue is taken up in CH$_2$Cl$_2$, the solution is filtered and the filtrate is washed with a small amount of NaHCO$_3$ solution. After stripping off the CH$_2$Cl$_2$, the excess 1,4-dichlorobutene is distilled off under 0.4 mm Hg and the residue (3.44 g) is chromatographed over silica gel in CH$_2$Cl$_2$/ethyl acetate (1:1). 2.4 g of an oil consisting of carbobenzoxyglycine 4-chloro-but-2-enyl ester are obtained.

EXAMPLE 33

18 g (0.1 mol) of C-phenylmalonic acid and 18 g (0.1 mol) of chloretone are reacted in the manner described in Example 28. Reprecipitating twice from methanol with water gives 11.7 g (35%) of white crystals of C-phenylmalonic acid mono-2,2,2-trichloro-tert.-butyl ester. Melting point = 76°-8° C.

EXAMPLE 34

4.46 g (20 mmols) of carbobenzoxy-L-alanine, 2.5 ml (22 mmols) of tert.-butylisonitrile and 1.96 ml (20 mmols) of chloral are reacted in the manner described in Example 32. Recrystallization of the product from CH$_2$Cl$_2$ with pentane gives 6.63 g (73%) of white crystals of carbobenzoxy-L-alanine 1-tert.-butylaminocarbonyl-2,2,2-trichloroethyl ester. Melting point = 114°-6° C. $[\alpha]_D^{25} = -24.0°$ ($c = 1.0$ in ethanol).

EXAMPLE 35a 18.3 g (50 mmols) of penicillin-V S-oxide are stirred with 12.5 g (60 mmols) of dicyclohexyl-carbodiimide in 250 ml of absolute CH$_2$Cl$_2$ at 0° C for 1 hour. After adding 50 ml (0.7 mol) of 2-bromoethanol, the mixture is stirred for 7 hours at 20° C. It is filtered, the filtrate is washed with 5% strength citric acid (at 0° C), H$_2$O and saturated NaHCO$_3$ solution and dried (Na$_2$SO$_4$) and the solvent is stripped off. After chromatography over silica gel 60 in CH$_2$Cl$_2$ and elution with acetone, 17.2 g of a pale yellow solid are obtained and this is identified by spectroscopy (NMR and IR) as penicillin-V S-oxide 2'-bromoethyl ester contaminated with dicyclohexylurea. No further purification effect was achieved by chromatographing again.

EXAMPLE 35b 120 g of penicillin V, 250 ml of 1,2-dibromoethane, 900 ml of DMSO and 84 g of anhydrous sodium carbonate are stirred at room temperature for 20 hours. 3 Liters of ice water and 2 liters of toluene are added and the organic fraction is extracted by shaking with bicarbonate solution and water. After drying over Na$_2$SO$_4$, the solution is concentrated and 300 ml of isopropanol/ether (2:1) are added. After 1 day it is possible to filter off 125 g of penicillin-V 2'-bromoethyl ester (melting point 130°-132° C). This ester (91 g) is dissolved in 450 ml of glacial acetic acid and 29 ml of 35% strength H$_2$O$_2$ are added in the course of 2 hours at below 33° C. After 20 hours the solution is concentrated in a rotary evaporator and 110 g of an oily penicillin-V S-oxide 2'-bromoethyl ester which still contains a little glacial acetic acid and is suitable for further reactions are obtained.

EXAMPLE 36

A solution of 61 g of penicillin-V bromoethyl ester S-oxide in a mixture of 220 ml of dimethylacetamide and 400 ml of toluene is warmed, with 2.4 g of tin-II methanesulphonate, to the reflux temperature for 1 hour and poured into ice water. The organic fraction is separated off, washed with water, dried and concentrated. Deacetoxy-cephalosporin-V bromoethyl ester, which has a melting point of 110°-112° C, is obtained from the residue (58 g) by purification over silica gel.

EXAMPLE 37

18.3 g (50 mmols) of penicillin-V S-oxide and 180 g (1.0 mol) of chloretone are reacted, and worked up, in the manner described in Example 35a. This gives 12.4 g of a pale yellow solid, which is identified by spectroscopy (NMR and IR) as penicillin-V S-oxide 2',2',2'-trichlor-tert.-butyl ester contaminated with dicyclohexylurea. It was not possible to further purify the substance by chromatographing again.

EXAMPLE 38

8.75 ml of a 45% strength aqueous solution of chloroacetaldehyde in 25 ml of tetrahydrofuran are added in the course of 10 minutes, at 0° C, to 18.3 g (50 mmols) of penicillin-V S-oxide and 6.25 ml (55 mmols) of tert.-butylisonitrile in 100 ml of tetrahydrofuran and the solution is stirred for a further 2 hours at 20° C. The solvent is stripped off, the residue is taken up in CH$_2$Cl$_2$, the solution is washed with 5% strength citric acid (at 0° C), H$_2$O and saturated NaHCO$_3$ solution and dried (Na$_2$SO$_4$) and the solvent is stripped off (21.5 g of crude product). After reprecipitating the product from CH$_2$Cl$_2$ with pentane, 15.2 g (58%) of crystals of analytically pure penicillin-V S-oxide 1'-tert.-butylaminocarbonyl-2'-chloroethyl ester are obtained. Melting point = 143°-7° C (decomposition). $[\alpha]_D^{25} = +104°$ ($c = 1.1$ in acetone).

EXAMPLE 39

1.47 g (1 ml, 10 mmols) of chloral in 5 ml of CH$_2$Cl$_2$ are added in the course of 10 minutes, at 0° C, to 3.66 g (10 mmols) of penicillin-V S-oxide and 1.25 ml (11 mmols) of tert.-butylisonitrile in 20 ml of absolute CH$_2$Cl$_2$ and the mixture is stirred for a further 2 hours at 20° C. The clear solution is washed with 5% strength citric acid (at 0° C), H$_2$O and saturated NaHCO$_3$ solution and dried (Na$_2$SO$_4$) and the solvent is stripped off, whereupon 5.9 g (99%) of a white solid consisting of penicillin-V S-oxide 1'-tert.-butylaminocarbonyl-2',2',2'-trichloroethyl ester, which is pure according to NMR spectroscopy and IR spectroscopy, are obtained. After reprecipitation from CH$_2$Cl$_2$ with pentane, 4.6 g (77%) of crystals of the analytically pure product are obtained. Melting point = 149°–51° C (decomposition). $[\alpha]_D^{25} = +139°$ ($c = 1$ in ethanol).

EXAMPLE 40

0.4 g of silver methanesulphonate is added to a solution of the ester (10 g) obtained according to Example 39 in 80 ml of dimethylacetamide and 200 ml of toluene and the mixture is warmed to the reflux temperature for 90 minutes, under a water separator, and is then poured into 600 ml of ice water. The same method of working up as in Example 36 gives a crude product which is used direct for ester splitting (see Example 73).

EXAMPLE 41

1.37 g (10 mmols) of 2-bromopropionaldehyde in 5 ml of $CH_2Cl_2$ are added in the course of 5 minutes, at 0° C, to 3.66 g (10 mmols) of penicillin-V S-oxide and 1.25 ml (11 mmols) of tert.-butylisonitrile in 20 ml of $CH_2Cl_2$ and the mixture is stirred for a further 4 hours at 20° C. It is washed at 0° C with 5% strength citric acid, water and saturated $NaHCO_3$ solution and dried ($Na_2SO_4$) and the solvent is stripped off. Recrystallization of the residue from $CH_2Cl_2$ with pentane gives 4.2 g (72%) of a solid consisting of penicillin-V S-oxide 1'-tert.-butylaminocarbonyl-2'-bromopropyl ester. Melting point = 136°–8° C. $[\alpha]_D^{25} = -100°$ ($c = 1.1$ in ethanol).

EXAMPLE 42

2.16 g (10 mmols) of 2,2-dibromopropionaldehyde (see Example 4a) in 5 ml of $CH_2Cl_2$ are added in the course of 10 minutes, at 0° C, to 3.66 g (10 mmols) of penicillin-V S-oxide and 1.25 ml (11 mmols) of tert.-butylisonitrile in 20 ml of absolute $CH_2Cl_2$ and the mixture is stirred for a further 6 hours at 20° C. The clear yellow solution is washed with 5% strength citric acid (at 0° C), $H_2O$ and saturated $NaHCO_3$ solution and dried ($Na_2SO_4$) and the solution is stripped off, whereupon 6.35 g (95%) of a white solid consisting of penicillin-V S-oxide 1'-tert.-butylaminocarbonyl-2',2'-dibromopropyl ester, which is pure according to NMR and IR spectroscopy, are obtained. After reprecipitation from $CH_2Cl_2$ with pentane, 4.45 g (67%) of crystals of the analytically pure product are obtained. Melting point = 138°–40° C (decomposition). $[\alpha]_D^{25} = +119°$ ($c = 0.6$ in ethanol).

EXAMPLE 43

The ester (7.5 g) obtained according to Example 42 is rearranged, as in Example 40, to give deacetoxycephalosporin-V 1'-tert.-butylaminocarbonyl-2',2'-dibromopropyl ester, which is obtained in 75% yield as an oily mixture of the two diastereomeric esters (center of asymmetry in the ester radical!). See Example 74 for splitting of the ester.

EXAMPLE 44

2.8 g (10 mmols) of bromal in 5 ml of $CH_2Cl_2$ are added in the course of 5 minutes, at 0° C, to 3.66 g (10 mmols) of penicillin-V S-oxide and 1.25 ml (11 mmols) of tert.-butylisonitrile and the mixture is stirred for a further 2 hours at 20° C. It is washed at 0° C with 5% strength citric acid, water and saturated $NaHCO_3$ solution and dried ($Na_2SO_4$) and the solvent is stripped off, whereupon 6.2 g (85%) of a solid consisting of penicillin-V S-oxide 1'-tert.-butylaminocarbonyl-2',2',2'-tribromoethyl ester are obtained. Recrystallization from $CH_2Cl_2$ with pentane gives white crystals. Melting point = 138°–44° C. $[\alpha]_D^{25} = +104°$ ($c = 1.1$ in DMSO).

EXAMPLE 45

6.53 g (20 mmols) of 2,2,2-trichloroethoxycarbonyl-D-C-phenylglycine and 10 ml of thionyl chloride are heated to 70° C for 1 hour. The solvent is stripped off and thionyl chloride is removed by evaporating 4 times with absolute tetrahydrofuran in a rotary evaporator. The oil is dissolved in 100 ml of absolute acetone and this solution is added dropwise, at −5 to 0° C, in the course of 5 minutes to a solution of 4.32 g (20 mmols) of 6-APA, 2.5 g (30 mmols) of $NaHCO_3$, 800 mg (20 mmols) of NaOH, 150 ml of $H_2O$ and 50 ml of acetone and the mixture is stirred for a further 30 minutes at 0° C. It is washed with a large amount of ether (4 × 250 ml) and the aqueous phase (pH = 8.8) is provided with a lower layer of $CH_2Cl_2$ and acidified, at 0° C, with 1 N HCl to a pH of 3.5. The aqueous phase is extracted a further 3 times with $CH_2Cl_2$, the combined $CH_2Cl_2$ extracts are washed with saturated NaCl solution and dried, the solvent is stripped off and the residue is dried under a high vacuum. This gives 9.5 g (90%) of a white solid which is characterized by spectroscopy (NMR and IR) as 2',2',2'-trichloroethoxycarbonyl-ampicillin. Melting point = 147°–50° C (decomposition). $[\alpha]_D^{25} = +114°$ ($c = 1.6$ in ethanol).

EXAMPLE 46

7.9 g (20 mmols) of 2,2-dibromopropoxycarbonyl-D-C-phenylglycine and 10 ml of thionyl chloride are heated to 70° C for 1 hour. The solvent is stripped off and the excess thionyl chloride is removed by stripping off five times with absolute THF. The oil is dissolved in 100 ml of absolute acetone and this solution is added dropwise, at 0° C, in the course of 5 minutes to a solution of 4.32 g (20 mmols) of 6-APA, 2.5 g (30 mmols) of $NaHCO_3$, 800 mg (20 mmols) of sodium hydroxide, 150 ml of water and 50 ml of acetone and the mixture is stirred for a further 30 minutes at 0° C. It is washed with ether (4 × 300 ml), 40 g of NaCl are added and the aqueous phase (pH 7.7) is covered with a layer of 200 ml of ethyl acetate. It is acidified to a pH of 3.5 with 1 N hydrochloric acid at 0° C and the aqueous phase is extracted with ethyl acetate (3 × 50 ml). The combined ethyl acetate extracts are washed with saturated NaCl solution (2 × 30 ml), concentrated to 50 ml and extracted with 15 ml of 1 M $NaHCO_3$ solution and then with 5 ml of water and the combined aqueous extracts are washed with ethyl acetate (4 × 20 ml). After freeze-drying, 8.5 g (69%) of a white solid consisting of the sodium salt of 2',2'-dibromopropoxycarbonyl-ampicillin are obtained. Decomposition above 180° C. $[\alpha]_D^{25} = +133°$ ($c = 1.4$ in water).

EXAMPLE 47

3.6 ml (45 mmols) of pyridine are added, at 0° C, to 4.8 g (23 mmols) of $PCl_5$ in 50 ml of $CH_2Cl_2$ and the mixture is stirred with 9.1 g (20 mmols) of cephalosporin-V 2'-bromoethyl ester for 1 hour at 0° C. 15 ml of n-propanol are added in the course of 2 minutes, at 0° C, to the clear reddish solution. After 30 minutes, the turbid solution is stirred vigorously at 0° C with 30 ml of saturated NaCl solution and 60 ml of petroleum ether, whereupon crystals form between the phases. After 10 minutes a further 60 ml of petroleum ether are added and the mixture is stirred for a further 15 minutes. After the product has been filtered off and washed with saturated NaCl solution until neutral, a pale brownish powder is obtained and this is dissolved in $H_2O$ and the solution is washed with ether and freeze-dried. This gives 7.3 g of white crystals of 7-ADCA 2'-bromoethyl ester-hydrochloride containing NaCl. Decomposition above 130° C.

EXAMPLE 48

1.04 g (0.86 ml, 11 mmols) of chloroformic acid methyl ester in 50 ml of absolute tetrahydrofuran are added dropwise, at −10° C, to 3.6 g (11 mmols) of 2,2,2-trichloroethoxycarbonyl-D-C-phenylglycine and 1.11 g (1.55 ml, 11 mmols) of triethylamine in 100 ml of absolute tetrahydrofuran and the mixture is stirred for a further 10 minutes. 3.58 g (10 mmols) of 7-ADCA 2'-bromoethyl ester-hydrochloride are added, 1.01 g (1.4 ml, 10 mmols) of triethylamine in 50 ml of absolute tetrahydrofuran are added dropwise in the course of 5 minutes and the mixture is stirred for a further 3 hours at −10° C. The solvent is stripped from the mixture, the residue is taken up in ethyl acetate, the solution is washed at 0° C with 5% strength citric acid, $H_2O$ and saturated $NaHCO_3$ solution and dried ($Na_2SO_4$) and the solvent is stripped off. The resulting oil crystallizes on grinding with pentane. After chromatography over silica gel in ethyl acetate and subsequent reprecipitation from ethyl acetate with hexane, 2.7 g (43%) of white crystals of 2',2',2'-trichloroethoxycarbonyl-cephalexin 2'-bromoethyl ester are obtained. Melting point = 128°-32° C. $[\alpha]_D^{25} = +72°$ ($c = 0.6$ in ethanol).

EXAMPLE 49

3.12 g (10 mmols) of phenylmalonic acid mono-trichloroethyl ester and 5 ml of thionyl chloride are heated to 70° C for 1 hour. The solvent is stripped off and the excess thionyl chloride is removed by stripping off four times with absolute THF. The oil is dissolved in 50 ml of absolute acetone and this solution is added dropwise in the course of 5 minutes, at 0° C, to a solution of 2.16 g (10 mmols) of 6-APA, 1.25 g (15 mmols) of $NaHCO_3$, 400 mg (10 mmols) of NaOH, 75 ml of water and 25 ml of acetone and the mixture is stirred for a further 30 minutes at 0° C. It is washed with ether (4 × 100 ml), the aqueous phase (pH = 8.4) is covered with a layer of 100 ml of ether and, at 0° C, is acidified with 1 N hydrochloric acid to a pH of 3.5 and the aqueous phase is extracted with ether (3 × 50 ml). The combined ether extracts are washed with saturated NaCl solution (2 × 30 ml) and extracted with 40 ml of 0.2 M $NaHCO_3$ solution. After freeze-drying of the extract, 2.3 g (43%) of a white solution consisting of the sodium salt of 2',2',2'-trichloroethyl carbenicillin are obtained. Decomposition above −170° C $[\alpha]_D^{25} = +142°$ ($c = 0.6$ in water).

EXAMPLE 50

6.79 g (20 mmols) of 2,2,2-trichloro-tert.-butylphenylmalonic acid and 10 ml of thionyl chloride are heated to 70° C for 1 hour. The solvent is stripped off and the excess thionyl chloride is removed by stripping off five times with absolute THF. The oil is dissolved in 100 ml of absolute acetone and this solution is added dropwise in the course of 5 minutes, at 0° C, to a solution of 4.32 g (20 mmols) of 6-APA, 2.5 g (30 mmols) of $NaHCO_3$, 800 mg (20 mmols) of sodium hydroxide, 150 ml of water and 50 ml of acetone and the mixture is stirred for a further 30 minutes at 0° C. It is washed with ether (4 × 300 ml), 40 g of NaCl are added and the aqueous phase (pH = 8.2) is covered with a layer of 200 ml of ether. It is acidified, at 0° C, with 1 N hydrochloric acid to a pH of 3.5 and the aqueous phase is extracted with ether (3 × 50 ml). The combined ether extracts are washed with saturated NaCl solution (2 × 30 ml), concentrated to 50 ml and extracted with 15 ml of 1 M $NaHCO_3$ solution and then with 5 ml of water and the combined aqueous extracts are washed with ether (2 × 20 ml). After freeze-drying, 6.95 g (60%) of a white solid consisting of the sodium salt of 2',2',2'-trichloro-tert.-butyl-carbenicillin are obtained. Decomposition above 150° C. $[\alpha]_D^{25} = +156°$ ($c = 1.1$ in water).

EXAMPLE 51

3.93 g (6.0 mmols) of N,O-di-(2',2'-dibromopropoxycarbonyl)-p-hydroxy-C-phenylglycine and 5 ml of thionyl chloride are heated to 70° C for 1 hour. The solvent is stripped off and the excess thionyl chloride is removed by stripping off four times with absolute THF. The resin is dissolved in 30 ml of absolute acetone and this solution is added dropwise in the course of 5 minutes, at 0° C, to a solution of 1.3 g (6.0 mmols) of 6-APA, 750 mg (9 mmols) of $NaHCO_3$, 240 mg (6 mmols) of NaOH, 45 ml of water and 15 ml of acetone and the mixture is stirred for a further 60 minutes at 0° C. It is washed with ether/petroleum ether (1:1) (2 × 50 ml), 20 ml of saturated NaCl solution are added in order to break the stable emulsion and the aqueous phase (from which an oil separates out, pH = 8.2) is covered with a layer of ethyl acetate and acidified, at 0° C, with 1 N hydrochloric acid to a pH of 3.5 and the aqueous phase is extracted a further 3 times with ethyl acetate. The combined ethyl acetate extracts (150 ml) are washed with 30 ml of saturated NaCl solution, 150 ml of petroleum ether are added and the mixture is extracted with 50 ml of 0.1 M $NaHCO_3$ solution, whereupon an oil separates out of the aqueous phase (pH = 7.9). After freeze-drying, 3.7 g (72%) of a white solid consisting of the sodium salt of di-(2',2'-dibromopropoxycarbonyl)-"hydroxyampicillin" are obtained. Decomposition above 200° C. $[\alpha]_D^{25} = +81.5°$ ($c = 1.1$ in water).

EXAMPLES 52 – 82

All the reactions with cobalt-I complexes, which are sensitive to oxygen, are carried out in an atmosphere of purified nitrogen using $N_2$-saturated solvents. The substrates (and additional reagents) are flushed with nitrogen before they are employed for the cleavage reaction. After the reaction has ended and excess cobalt-I complex has been destroyed, further working up is carried out in air. The cobalt-II complexes, which are obtained quantitatively, can be re-used again to prepare cobalt-I complexes.

EXAMPLE 52

Lithium cobalt-(I)-phthalocyanine Li[PcCo]. 4.5 THF 36 g (0.2 mol) of benzophenone and 10 g of lithium, which has been cut into small pieces, in 600 ml of absolute THF are shaken for 4 hours at 20° C, in a $N_2$ atmosphere, in a G0 frit which has been drawn out into a dropping funnel and has a tap connection. The deep red di-lithium benzophenone solution is allowed to run (in the course of 10 minutes, with pressure equalization) out of the frit into a suspension of 171 g (0.3 mol) of cobalt phthalocyanine in 500 ml of absolute THF, while stirring, and the mixture is allowed to cool to 20° C. The dark green crystals of Li[PcCo]. 4.5 THF are filtered off on a G2 frit, washed 3 times with absolute THF and dried under 0.1 mm Hg. Yield: 245 g (91%). The lithium cobalt-(I)-phthalocyanine can be stored at room temperature. NMR spectrum in $d_6$-DMSO (e-TMS): $\delta$ = 1.98 (quint, THF); 3.87 (t, THF); 8.33 (quart, J = 3 Hz, Pc); 9.38 (quart, J = 3 Hz, Pc). THF content: 4.5 (from the NMR spectrum). Li content: calculated 0.774 found 0.77% (acidimetrically from the hydrolysis product of lithium cobalt-(I)-phthalocyanine). Oxidation value: 1.02 reduction equivalents (iodometrically).

EXAMPLE 53

Acetone solution of sodium cobalt-(I)-phthalocyanine 9.7 g of 1.62% strength sodium amalgam (6.8 mmols of sodium) and 4.0 g (7.0 mmols) of cobalt phthalocyanine are stirred vigorously for 1 hour in 50 ml of absolute acetone. A deep green clear solution is obtained and, after leaving to stand for 6 hours at 20° C, this is decanted off from the mercury and employed for cleavage reactions. The solution is 0.15 molar in respect of sodium cobalt-phthalocyanine.

EXAMPLE 54

Sodium cobalt-phthalocyanine in acetonitrile 35 g (61 mmols) of cobalt-phthalocyanine in 300 ml of absolute acetonitrile are stirred vigorously for 1 hour at 20° C with 23 g of 5% strength sodium amalgam (50 mmols of sodium). The deep green solution contains 0.07 mol/l of sodium cobalt-phthalocyanine.

EXAMPLE 55

Sodium bis-[2-(1'-imino-3'-isoindolenine)-5-amino-1,3,4-thiadiazolato]-cobaltate-I in methanol:

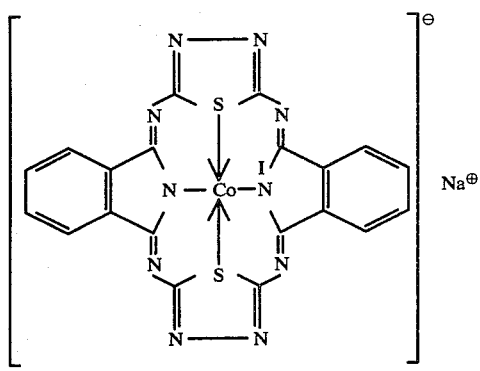

30 mg of bis-[2-(1'-imino-3'-isoindolenine)-5-amino-1,3,4-thiadiazolato]-cobalt-II are added to 2 g (50 mmols) of sodium borohydride in 40 ml of methanol at 0° C, while stirring. The green solution contains a catalytic amount of sodium bis-[2-(1'-imino-3'-isoindolenine)-5-amino-1,3,4-thiadiazolato]-cobaltate-I in methanol.

EXAMPLE 56

6.95 g (7.7 mmols) of lithium cobalt-phthalocyanine in 50 ml of methanol are stirred at 20° C with 890 mg (3.0 mmols) of 2-bromoethoxycarbonyl-L-alanine tert.-butyl ester until the evolution of ethylene has ended after about 2 hours. 6 g (30 mmols) of citric acid in 20 ml of water are added at 0° C and the $CO_2$ escapes in the course of 2 minutes. The mixture is left to stand for 20 minutes and is filtered through a PcC filter, the material on the filter is rinsed with water and methanol and the methanol is stripped off from the filtrate and the residue is washed with ether (stripping of the ether extracts gives only traces of PcC). The aqueous solution is neutralized with about 15 g of $NaHCO_3$ and extracted 3 times with $CH_2Cl_2$, the $CH_2Cl_2$ extracts are dried ($Na_2SO_4$) and the solvent is stripped off, whereupon 350 mg (81%) of L-alanine tert.-butyl ester are obtained. Boiling point$_{10}$ = 52° C $[\alpha]_D^{25}$ = +3.2° (c = 1.5 in ethanol).

EXAMPLE 57

7.7 g (8.5 mmols) of lithium cobalt-phthalocyanine in 50 ml of methanol are stirred with 846 mg (3.0 mmols) of 2-bromoethoxycarbonyl-L-valine methyl ester for 2 hours at 20° C (end of the evolution of ethylene) and the mixture is worked up as described in Example 56. 300 mg (76%) of L-valine methyl ester are obtained. Boiling point$_{10}$ = 53° C. $[\alpha]_D^{25}$ = +42.2° (c = 0.7 in ethanol).

EXAMPLE 58

12 g (13.3 mmols) of lithium cobalt-phthalocyanine in 50 ml of methanol are stirred, at 15° – 20° C, with 1.62 (5.0 mmols) of 2-bromoethoxycarbonyl-L-valine tert.-butyl ester until the evolution of ethylene has ended after about 1 hour. 50 ml of 5% strength citric acid are added, at 0° C, to the deep green colored reaction mixture and the resulting mixture is stirred for a further 10 minutes (evolution of $CO_2$). After leaving to stand for one hour, the mixture is filtered through a G3 frit to remove PcC, the material on the filter is rinsed with water and the filtrate is neutralized with $NaHCO_3$ and extracted with ether. The extracts are washed with a little water and dried ($Na_2SO_4$) and the solvent is stripped off, whereupon 770 mg (89%) of L-valine tert.-butyl ester are obtained. Boiling point$_1$ = 45° C. $[\alpha]_D^{25}$ = +32.5° (c = 2, in ethanol).

EXAMPLE 59

7.6 g (8.4 mmols) of lithium cobalt-phthalocyanine in 30 ml of methanol are stirred with 1.1 g (3.0 mmols) of 2-bromoethoxycarbonyl-L-alaninyl-L-valine tert.-butyl ester for 50 minutes at 15° – 20° C and the mixture is worked up as described in Example 58. 600 mg (82%) of oil consisting of L-alaninyl-L-valine tert.-butyl ester, which crystallizes slowly, are obtained. Melting point = 31–3° C. $[\alpha]_D^{25}$ = −21.0° (c = 1.9 in ethanol).

EXAMPLE 60

5.2 g (5.8 mmols) of lithium cobalt-phthalocyanine in 30 ml of methanol are stirred with 700 mg (1.5 mmols) of 2-bromoethoxycarbonyl-L-alaninyl-L-valinyl-L-alanine tert.-butyl ester at 20° C until the evolution of ethylene (29 ml) has ended after 1 hour. 3 g (15 mmols) of citric acid in 30 ml of water are added at 0° C and the mixture is stirred for a further 5 minutes (evolution of 25 m of $CO_2$) and then allowed to stand for 10 minutes. The blue PcC precipitate is filtered off on a suction filter and rinsed with water and methanol, the organic solvent is stripped off from the filtrate and the residue is washed with $CH_2Cl_2$ (stripping of the $CH_2Cl_2$ extracts gives only traces of PcC). The aqueous solution is neutralized with $NaHCO_3$ and extracted with a large amount of $CH_2Cl_2$, the extracts are dried ($Na_2SO_4$) and the solvent is stripped off, whereupon a slightly green colored (PcCO) oil is obtained. For purification, this oil is taken up in 5% strength citric acid, the mixture is filtered, the filtrate is washed with $CH_2Cl_2$, neutralized with $NaHCO_3$ and extracted with a large amount of ethyl acetate, the extracts are dried and the solvent is stripped off. Repreciptation of the product from ethyl acetate with hexane gives 380 mg (80%) of white needles of L-alaninyl-L-valinyl-L-alanine tert.-butyl ester, melting point = 88° C. $[\alpha]_D^{25} = -59.0°$ ($c = 1$ in ethanol).

EXAMPLE 61

5.25 g (5.8 mmols) of lithium cobalt-phthalocyanine in 30 ml of methanol and 834 mg (2.0 mmols) of 2,2-dibromopropoxycarbonyl-L-valine tert.-butyl ester are stirred for 30 minutes at 20° C. 4 g (20 mmols) of citric acid in 20 ml of water are added, at 0° C, to the deep green reaction mixture and the resulting mixture is stirred for a further 5 minutes and allowed to stand for 15 minutes. The cobalt-phthalocyanine is filtered off and the filtrate is washed with a little ether, neutralized with NaHCO$_3$ and extracted with CH$_2$Cl$_2$. The combined CH$_2$Cl$_2$ extracts are washed with saturated NaCl solution and dried (Na$_2$SO$_4$) and the solvent is stripped off. This gives 267 mg (77%) of L-valine tert.-butyl ester. Boiling point$_{10}$ = 74° C. $[\alpha]_D^{25} = +32.6°$ ($c = 2,2$ in ethanol).

EXAMPLE 62

8.0 g (8.9 mmols) of lithium cobalt-phthalocyanine in 45 ml of methanol are stirred, at 15° – 20° C, with 1.22 g (3.5 mmols) of 2,2,2-trichloroethoxycarbonyl-L-valine tert.-butyl ester (no evolution of gas). After 5 minutes a colorless solution with a blue precipitate of PcC is obtained. 4 g of citric acid in 30 ml of water are added at 0° C (evolution of CO$_2$), PcC is filtered off on a suction filter and rinsed with water and acetone, the solvent is stripped from the organic solution and the residue is washed with CH$_2$Cl$_2$ (working up of the CH$_2$Cl$_2$ extracts gives a trace of 2,2,2-trichloroethoxycarbonyl-L-valine tert.-butyl ester). The product is neutralized with NaHCO$_3$ and extracted with CH$_2$Cl$_2$, the extracts are dried (Na$_2$SO$_4$) and the solvent is stripped off, whereupon 550 mg (91%) of L-valine tert.-butyl ester are obtained. Boiling point$_{10}$ = 73° C. $[\alpha]_D^{25} = +32.2°$ ($c = 1.1$ in ethanol).

EXAMPLE 63

5.4 g (6.0 mmols) of lithium -cobalt-phthalocyanine in 30 ml of absolute acetone, 1 g (about 10 mmols) of phenol and 700 mg (2.0 mmols) of 2,2,2-trichloroethoxycarbonyl-L-valine tert.-butyl ester are stirred for 1 hour at 20° C. 10 ml of water saturated with CO$_2$ are added to the deep green solution, CO$_2$ and air are passed into the mixture for 5 minutes and the mixture is left to stand for 30 minutes. Cobalt phthalocyanine is filtered off and rinsed with water and acetone, the acetone is stripped off from the filtrate and the residual aqueous phase is extracted with CH$_2$Cl$_2$. Stripping of the combined CH$_2$Cl$_2$ extracts (after drying over Na$_2$SO$_4$) gives L-valine tert.-butyl ester which is contaminated with traces of PcC and contains diacetone alcohol. Purification via the hydrocitrate gives 260 mg (75% yield).

EXAMPLE 64

4.6 g (5.1 mmols) of lithium cobalt-phthalocyanine in 25 ml of methanol, 1 g (about 10 mmols) of phenol and 592 mg (2.0 mmols) of tert.-butoxycarbonyl-L-alanine 2-bromoethyl ester are stirred for 5 minutes at 20° C (46 ml of ethylene). 20 ml of water saturated with CO$_2$ are added to the deep green solution at 0° C, CO$_2$ and air are passed into the mixture for 5 minutes and the precipitate of cobalt-phthalocyanine is allowed to settle for 30 minutes. The PC is filtered off and rinsed with water (3 × 10 ml), the filtrate (pH = 8.5) is washed with ether (4 × 30 ml), provided with a lower layer of 30 ml of CH$_2$Cl$_2$ and acidified at 0° C with 1 N HCl to a pH of 2.5 and the aqueous phase is extracted with CH$_2$Cl$_2$ (3 × 20 ml). The combined CH$_2$Cl$_2$ extracts are washed with saturated NaCl solution (2 × 10 ml) and dried (Na$_2$SO$_4$) and the solvent is stripped off. Recrystallization of the residue from ethyl acetate with hexane gives 215 mg (57%) of white crystals of tert.-butoxycarbonyl-L-alanine. Melting point = 80-1° C. $[\alpha]_D^{25} \times -22°$ ($c = 0.5$ in glacial acetic acid).

EXAMPLE 65

5.1 g (5.6 mmols) of lithium cobalt-phthalocyanine in 30 ml of methanol, 1 g (about 10 mmols) of phenol and 887 mg (2.0 mmols) of tert.-butoxycarbonyl-L-phenylalaninyl-L-alanine-2-bromoethyl ester are stirred for 1 hour at 20° C (38.5 ml of ethylene). 3 g of KH$_2$PO$_4$ in 20 ml of water are added to the deep green solution at 0° C and the PcC is filtered off. The filtrate (pH = 6.1) is washed with CH$_2$Cl$_2$*, acidified with 1 N HCl at 0° C to a pH of 3.0 and extracted with a large amount of CH$_2$Cl$_2$. When the CH$_2$Cl$_2$ extracts are dried (Na$_2$SO$_4$) and the solvent is stripped off, 460 mg of a white solid are obtained (fraction 1).

*The solvent is stripped from the phenol-containing CH$_2$Cl$_2$ wash phase and the residue is taken up in ether and extracted with NaHCO$_3$ solution. The extracts are washed with ether, acidified at 0° C with 1 N HCl to a pH of 2.5 and extracted with CH$_2$Cl$_2$, the CH$_2$Cl$_2$ extracts are dried (Na$_2$SO$_4$) and the solvent is stripped off, whereupon 130 mg of a white solid are obtained (fraction 2). Repreciptation of the combined fractions (1 + 2) from CH$_2$Cl$_2$ with pentane gives 570 mg (85%) of white crystals of tert.-butoxycarbonyl-L-phenylalaninyl-L-alanine. Melting point = 150° C. $[\alpha]_D^{25} = -1.7°$ ($c = 1.1$ in ethanol).

EXAMPLE 66

5.3 g (5.9 mmols) of lithium cobalt-phthalocyanine in 30 ml of methanol, 1 g (about 10 mmols) of phenol and 1.1 g (2.0 mmols) of carbobenzoxy-L-alaninyl-L-phenylalaninyl-L-alanine 2-bromoethyl ester are stirred for 40 minutes at 20° C and the mixture is worked up as described in Example 64. 740 mg (84%) of a white solid consisting of carbobenzoxy-L-alaninyl-L-phenylalaninyl-L-alanine are obtained. Repreciptation from methanol with water gives white crystals. Melting point = 174°-6° C. $[\alpha]_D^{25} = -18.3°$ ($c = 1.0$ in glacial acetic acid).

EXAMPLE 67

8.3 g (9.2 mmols) of lithium cobalt-phthalocyanine in 50 ml of methanol, 2 g (about 20 mmols) of phenol and 1.69 g (3.0 mmols) of tert.-butoxycarbonyl-L-phenylalanine-1-tert.-butylaminocarbonyl-2,2-dibromopropyl ester are stirred for 1 hour at 20° C. 1.5 g (11 mmols) of KH$_2$PO$_4$ in 10 ml of water are added to the deep green solution at 0° C and the PcC is filtered off. The filtrate is washed with CH$_2$Cl$_2$ and the CH$_2$Cl$_2$ phase is extracted with N HCO$_3$ solution. The combined aqueous phases are washed with ether, acidified at 0° C with 1 N HCl to a pH of 3.0 and extracted with CH$_2$Cl$_2$. When the extracts are dried (Na$_2$SO$_4$) and the solvent is stripped off, 520 mg (65%) of a colorless resin consisting of tert.-butoxycarbonyl-L-phenylalanine are obtained. Reprecipitation from ethyl acetate with hexane gives white crystals. Melting point = 84° - 6° C. [α]$_D^{25}$ = +26.2° (c = 1.9 in methanol).

EXAMPLE 68

5.35 g (5.9 mmols) of lithium cobalt-phthalocyanine in 30 ml of absolute acetone, 1 g (about 10 mmols) of phenol and 910 mg (2.0 mmols) of carbobenzoxy-L-alanine 1-tert.-butylaminocarbonyl-2,2,2-trichloroethyl ester are stirred for 30 minutes at 20° C and the mixture is worked up as described in Example 64. Digesting with pentane gives 265 mg (59%) of white needles of carbobenzoxy-L-alanine. Melting point = 84°-5° C. [α]$_D^{25}$ = −13.2° (c = 1.3 in ethanol).

EXAMPLE 69

5.5 g (6.1 mmols) of lithium cobalt-(I)-phthalocyanine in 30 ml of acetonitrile, 1.2 g (12 mmols) of phenol and 595 mg (2.0 mmols) of carbobenzoxy-glycine 4-chlorobut-2-enyl ester are stirred for 10 minutes at 20° C. 30 ml of water saturated with CO$_2$ are added to the deep green mixture at 0°, CO$_2$ and air are passed in for 5 minutes and the mixture is left to stand for 30 minutes. After filtering off the cobalt-II phthalocyanine, the filtrate is washed with ether, NaCl is added and the mixture is acidified with half-concentrated hydrochloric acid. It is then extracted with CH$_2$Cl$_2$, the extracts are washed with a little NaCl solution and dried (Na$_2$SO$_4$) and the solvent is stripped off, whereupon 338 mg (80%) of a white solid consisting of carbobenzoxy-glycine are obtained. Melting point = 118° C.

EXAMPLE 70

37 ml of 0.07 M sodium cobalt-phthalocyanine solution (2.6 mmols) in acetontrile are stirred with 500 mg (about 5 mmols) of phenol and 457 mg (1.0 mmol) of penicillin-V 2-bromoethyl ester for 4 hours at 20° C (19 ml of ethylene evolved during this time). 40 ml of water saturated with CO$_2$ are added to the deep green mixture at 0° C and CO$_2$ and air are blown through for 5 minutes. After filtering off the cobalt-II phthalocyanine, the filtrate is washed with ether, pH = 7.4, and provided with a lower layer of CH$_2$Cl$_2$. It is acidified at 0° C with 1 N HCl to a pH of 3.5, the aqueous phase is extracted with CH$_2$Cl$_2$, the combined CH$_2$Cl$_2$ extracts are washed with a little saturated NaCl solution and dried (Na$_2$SO$_4$) and the solvent is stripped off. This gives 230 mg (66%) of a white solid which consists of penicillin V which is pure according to spectroscopy (NMR and IR) and thin layer chromatography. [α]$_D^{25}$ = +172° (c = 0.6 in ethanol).

EXAMPLE 71

5.8 g (6.4 mmols) of lithium cobalt-I-phthalocyanine and 1 g (about 10 mmols) of phenol in 30 ml of absolute acetone are stirred with 1.19 g (2.0 mmols) 9f penicillin-V S-oxide 1-tert.-butylaminocarbonyl-2',2',2'-trichloroethyl ester for 1 hour at 20° C. 30 ml of H$_2$O saturated with CO$_2$ are added to the deep green reaction mixture at 0° C, CO$_2$ and air are blown through the mixture for 5 minutes and the mixture is left to stand for 1 hour. The cobalt-II phthalocyanine is filtered off and rinsed with H$_2$O, the filtrate is washed with ether (pH = 8.4), the clear colorless solution (50 ml) is covered with a layer of ethyl acetate and acidified at 0° C with 1 N HCL to a pH of 3.0, the aqueous phase is extracted with ethyl acetate, the combined ethyl acetate extracts are washed with saturated NaCl solution and dried (Na$_2$SO$_4$) and the solvent is stripped off. After washing hexane, 450 mg (62%) of white crystals of penicillin-V S-oxide which is pure according to spectroscopy (NMR and IR) are obtained. Reprecipitation from methanol/acetone (2:1) with H$_2$O gives an analytically pure product. Melting point = 150° C. [α]$_D^{25}$ = +173° (c = 0.5 in ethanol).

EXAMPLE 72

9.4 g (10.4 mmols) of lithium-cobalt-(I)-phthalocyanine and 2 g (about 20 mmols) of phenol in 50 ml of methanol are stirrred with 1.82 g (4.0 mmols) of deacetoxy-cephalosporin-V 2'-bromoethyl ester at 20° C until the escape of ethylene has ceased after 30 minutes. 6 g of KH$_2$PO$_4$ in 30 ml of water are added to the deep green reaction mixture at 0° C, the blue precipitate of PcC is allowed to settle at 20° C for 10 minutes and is filtered off on a suction filter and rinsed with water and the filtrate (pH = 6.0) is washed with CH$_2$Cl$_2$. The aqueous phase is acidified with 1 N HCl to a pH of 3.0 and extracted with CH$_2$Cl$_2$ and the extracts are dried (Na$_2$SO$_4$), concentrated and covered with a layer of pentane, whereupon white crystals of deacetoxy-cephalosporin V, which is pure according to spectroscopy (NMR and IR), are obtained. Recrystallization from water/methanol (1:1) gives an analytically pure product. Yield: 960 mg (69%). Melting point = 177° C (decomposition) [α]$_D^{25}$ = +170° (c = 0.45 in ethanol).

EXAMPLE 73

5.65 g (6.3 mmols) of lithium cobalt-phthalocyanine in 30 ml of absolute acetone, 1.3 g (13 mmols) of phenol and 1.16 g of deacetoxy-cephalosporin-V 1'-tert.-butylaminocarbonyl-2',2',2'-trichloroethyl ester (the still impure rearrangement product obtained from penicillin-V S-oxide 1'-tert.-butoxyaminocarbonyl-2',2',2'-trichloroethyl ester and chromatographed over silica gel) are stirred for 10 minutes at 20° C. 20 ml of water saturated with CO$_2$ are added at 0° C, CO$_2$ and air are blown through the mixture for 5 minutes and after 1 hour the PcCo is filtered off. The filtrate (100 ml) is washed with ether (4 × 50 ml), pH = 8.2, provided with a lower layer of CH$_2$Cl$_2$, acidified at 0° C with 1 N hydrochloric acid to a pH of 3.5 and again extracted with CH$_2$Cl$_2$. The combined CH$_2$Cl$_2$ extracts are washed with saturated NaCl solution and dried (Na$_2$SO$_4$) and the solvent is stripped off. 210 mg of a white solid which contains about 50% (comparison by thin layer chromatography) of deacetoxy-cephalosporin-V characterized by spectroscopy (NMR and IR) are obtained.

EXAMPLE 74

50 ml of a 0.07 M solution of sodium cobalt-phthalocyanine in acetonitrile, 1 g (10 mmols) of phenol and 1.0 g of deacetoxy-cephalosporin V 1'-tert.-butylaminocarbonyl-2',2'-dibromopropyl ester (crude product obtained from the rearrangement of penicillin-V S-oxide 1'-tert.-butylaminocarbonyl-2',2'-dibromopropyl ester) are stirred for 1 hour at 20° C. 30 ml of water saturated with $CO_2$ are added to the green mixture at 0° C, $CO_2$ and air are passed in for 5 minutes and after 1 hour the PcC is filtered off. The filtrate (100 ml) is washed with ether (4 × 50 ml), pH = 8.5, 20 g of NaCl are added, the mixture is provided with a lower layer of $CH_2Cl_2$, acidified at 0° C with 1 N hydrochloric acid to a pH of 3.5 and again extracted with $CH_2Cl_2$. The combined $CH_2Cl_2$ extracts are washed with saturated NaCl solution and dried ($Na_2SO_4$) and the solvent is stripped off. This gives 280 mg of a brownish solid which contains about 60% (comparison by thin layer chromatography) of deacetoxy-cephalosporin V characterized by spectroscopy (NMR and IR).

EXAMPLE 75

6.7 g (7.4 mmols) of lithium cobalt-phthalocyanine in 40 ml of absolute acetonitrile, 1.5 g (15 mmols) of phenol and 1.06 g (2.0 mmols) of the sodium salt of the 2',2',2'-trichloroethyl-carbenicillin are stirred for 1 hour at 20° C. 30 ml of water saturated with $CO_2$ are added to the deep green mixture at 0° C, $CO_2$ and air are passed in for 5 minutes and after 1 hour the PcC is filtered off. The filtrate (100 ml) is washed with ether (4 × 50 ml), pH = 8.7, 20 g of NaCl are added and the mixture is provided with a lower layer of $CH_2Cl_2$ and acidified at 0° C with 1 N hydrochloric acid to a pH of 2.0 and immediately again extracted with $CH_2Cl_2$. The combined $CH_2Cl_2$ extracts are washed with saturated NaCl solution (2 × 20 ml) and dried ($Na_2SO_4$) and the solvent is stripped off. This gives 415 mg (62%) of a white solid consisting of carbenicillin which contains phenylmalonic acid and is characterized by spectroscopy (NMR and IR).

EXAMPLE 76

3.9 g (4.3 mmols) of lithium cobalt-phthalocyanine in 20 ml of absolute acetonitrile, 1 g (10 mmols) of phenol and 800 mg (1.5 mmols) of the sodium salt of 2',2',2'-trichloroethyl-carbenicillin are stirred for 30 minutes at 20° C. 20 ml of water saturated with $CO_2$ are added to the deep green mixture at 0° C, $CO_2$ and air are passed in for 5 minutes and after 1 hour the PcC is filtered off. The filtrate (50 ml) is washed with ether (4 × 30 ml), pH = 8.8, neutralized (pH = 6.5) with 1 N hydrochloric acid and freeze-dried. This gives 750 mg of a white solid consisting of the disodium salt of carbenicillin (NMR, IR and thin layer chromatography).

EXAMPLE 77

6.2 g (6.9 mmols) of lithium cobalt-(I)-phthalocyanine in 35 ml of acetonitrile are stirred with 1.4 g (14 mmols) of phenol and 1.16 g (2.0 mmols) of the sodium salt of 2',2',2'-trichloro-tert.-butyl-carbenicillin for 15 minutes at 20° C. 20 ml of water saturated with $CO_2$ are added to the deep green mixture at 0° C, $CO_2$ and air are blown in for 5 minutes and the mixture is left to stand for 30 minutes. The cobalt-II phthalocyanine is filtered off and rinsed with water (2 × 15 ml) and the filtrate (50 ml, pH = 8.8) is washed with ether (4 × 30 ml), neutralized (pH = 6.5) with 1 N hydrochloric acid and freeze-dried. After drying over KOH/, 1.05 g of a white solid consisting of the disodium salt of carbenicillin (NMR, IR and thin layer chromatography) are obtained.

EXAMPLE 78

5.3 g (5.9 mmols) of lithium cobalt-phthalocyanine in 30 ml of absolute acetonitrile, 1.2 g (12 mmols) of phenol and 1.1 g (2.0 mmols) of the sodium salt of 2',2',2'-trichloroethoxycarbonyl-ampicillin are stirred for 30 minutes at 20° C. 20 ml of water saturated with $CO_2$ are added to the deep green mixture at 0° C, $CO_2$ and air are passed into the mixture for 5 minutes and after 30 minutes the PcC is filtered off. The filtrate (100 ml) is washed with ether (4 × 50 ml), pH = 9.5, neutralized (pH = 6.5) with 1 N hydrochloric acid and freeze-dried, whereupon 1.05 g of a greenish solid are obtained. This is dissolved in 2 ml of saturated $NaHCO_3$ solution, the solution is filtered, 500 mg of NaCl are dissolved in the yellow filtrate (3.5 ml, pH = 8.5), the resulting solution is acidified with 1 N hydrochloric acid to a pH of 4.5 (7.5 ml of solution) and the product is allowed to crystallize out at −20° C for 4 days. After the crystals have been filtered off and dried, 150 mg of a gray solid consisting of ampicillin, characterized by spectroscopy (NMR and IR) and by comparison by thin layer chromatography, are obtained. The mother liquor contains a further amount of ampicillin (comparison by thin layer chromatography).

EXAMPLE 79

5.8 g (6.4 mmols) of lithium cobalt-(I)-phthalocyanine in 30 ml of acetonitrile are stirred with 1.3 g (13 mmols) of phenol and 1.19 g (2.0 mmols) of the sodium salt of 2',2'-dibromopropoxycarbonyl-ampicillin for 15 minutes at 20° C. 20 ml of water saturated with $CO_2$ are added to the deep green mixture at 0° C, $CO_2$ and air are blown in for 5 minutes and the mixture is left to stand for 30 minutes. The cobalt-II phthalocyanine is filtered off and rinsed with water (2 × 10 ml) and the filtrate (50 ml, pH = 9.1) is washed with ethyl acetate (2 × 15 ml) and ether (2 × 15 ml), neutralized (pH = 6.8) with 1 N hydrochloric acid and freeze-dried, whereupon 1.2 g of a solid consisting of the sodium salt of ampicillin (NMR, IR and thin layer chromatography) are obtained.

This solid is dissolved in 2.0 ml of water, 500 mg of NaCl are added to the solution, the pH is brought to 4.6 with 1 N hydrochloric acid and the mixture is left to stand for 6 hours at −20° C. After the product has been filtered off, washed with saturated NaCl solution and dried over KOH/ 730 mg of ampicillin (thin layer chromatography, IR and NMR) are obtained.

EXAMPLE 80

11.85 g (13.1 mmols) of lithium cobalt-(I)-phthalocyanine in 100 ml of acetonitrile are stirred with 2.6 g (26 mmols) of phenol and 1.26 g (2.0 mmols) of 2',2',2'-trichloroethoxycarbonyl-cephalexin 2"-bromoethyl ester for 3 hours at 20° C (44 ml of ethylene). 40 ml of water saturated with $CO_2$ are added to the deep green viscous mixture at 0° C, $CO_2$ and air are blown in for 5 minutes and the mixture is left to stand for 1 hour. The cobalt-II phthalocyanine is filtered off and the filtrate (100 ml, pH = 9.2) is washed with ether (4 × 50 ml), neutralized (pH = 6.5) with 1 N hydrochloric acid and freeze-dried, whereupon 870 mg of a yellow solid consisting of the sodium salt of cephalexin (NMR) are obtained.

This solid is dissolved in 2 ml of water, the solution is filtered, 500 mg of NaCl are added to the filtrate, the pH is brought to 4.5 with 1 N hydrochloric acid and a small amount of brown precipitate is filtered off, the filtrate is shaken thoroughly with 5 ml of acetonitrile and the mixture is left to stand for 20 days at −20° C. After the product has been filtered off, washed with saturated NaCl solution and dried over KOH/ 125 mg of cephalexin (thin layer chromatography and IR) are obtained.

EXAMPLE 81

10.5 g (11.6 mmoles of lithium cobalt-(I)-phthalocyanine in 70 ml of acetonitrile are stirred with 2.3 g (23 mmols) of phenol and 1.75 g (2.0 mmols) of the sodium salt of N,O-di-(2',2'-dibromopropoxycarbonyl)-"hydroxyampicillin" for 15 minutes at 20° C. 50 ml of water saturated with $CO_2$ are added to the deep green mixture at 0° C, $CO_2$ and air are blown in for 5 minutes and the mixture is left to stand for 30 minutes. The cobalt-II phthalocyanine is filtered off and rinsed with water (2 × 25 ml) and the filtrate (100 ml, pH = 9.0) is washed with ether (4 × 40 ml), neutralized (pH = 6.5) with 1 N hydrochloric acid and freeze-dried, whereupon 1.6 g of a brownish solid consisting of the sodium salt of hydroxyampicillin (NMR and IR) are obtained.

This solid is dissolved in 2.5 ml of water, the solution is filtered, 500 mg of NaCl are added to the filtrate, the pH is brought to 4.5 with 1 N hydrochloric acid and the mixture is left to stand for 6 hours at −20° C. After the product has been filtered off, washed with saturated NaCl solution and dried over KOH/ 245 mg of hydroxyampicillin (thin layer chromatography, IR and NMR) are obtained. The mother liquor contains hydroxyampicillin (thin layer chromatography).

EXAMPLE 82

Bis-[2-(1'-imino-3'-isoindolenine)-5-amino-1,3,4-thiadiazolato] cobaltate-II is added, in an amount sufficient to cover the tip of a spatula, to 2 g (50 mmols) of sodium borohydride in 40 ml of methanol at 0° C, while stirring.

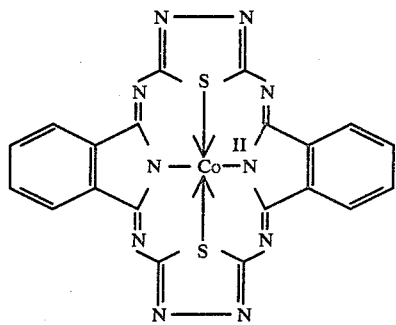

Without further cooling, 1.0 g (3.09 mmols) of 2-bromoethoxycarbonyl-L-valine tert.-butyl ester is added to the green solution which is thus obtained. Warming and a vigorous evolution of gas takes place immediately, the reaction mixture developing a brown coloration. After 10 minutes, the mixture is poured into 100 ml of water, the resulting mixture is filtered, the filtrate is acidified with citric acid and filtered again and the second filtrate is washed with $CH_2Cl_2$. After neutralizing the aqueous phase with $NaHCO_3$, this phase is extracted with $CH_2Cl_2$, the extracts are dried ($Na_2SO_4$) and the solvent is stripped off, whereupon 420 mg (80%) of L-valine tert.-butyl ester are obtained.

EXAMPLE 83

2.0 g (53 mmols) of sodium borohydride are dissolved in 100 ml of methanol at −35° C and bis-[2-(1'-imino-3'-isoindolenine)-5-amino-1,3,4-thiadiazolato] cobalt-II

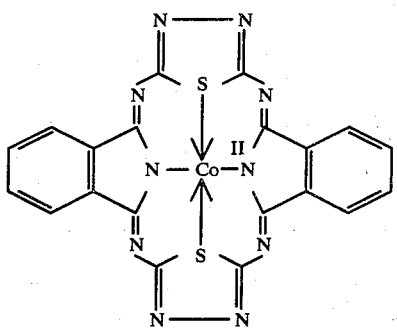

is added in an amount sufficient to cover the tip of a spatula (30 mg). After 3 minutes, 914 mg (2.0 mmols) of penicillin V 2'-bromoethyl ester in 10 ml of THF are added to the blue solution. At −20° C a vigorous evolution of gas takes place and after 10 minutes, while cooling the reaction solution to −20 to −10° C, this has ceased. 10 ml of acetone and, subsequently, 50 ml of ice-water saturated with $CO_2$ are added to the brown-green solution at −25° C, the temperature rising to −5° C when the addition is made, and $CO_2$ is passed into the solution at −10° C for 5 minutes. The clear green solution is washed 4 times with ether and the yellow aqueous phase (100 ml, pH = 8.5) is provided with a lower layer of $CH_2Cl_2$ and acidified at 0° C with 1 N HCl to a pH of 3.5. It is extracted a further 3 times with $CH_2Cl_2$, the combined $CH_2Cl_2$ extracts are washed with saturated NaCl solution and dried ($Na_2SO_4$) and the solvent is stripped off; 210 mg of a greenish-tinged solid consisting of penicillin V (NMR, IR and comparison by thin layer chromatography) are obtained. $[\alpha]_D^{25} = +151°$ (c = 0.8 in ethanol).

EXAMPLE 84

178 g (1.0 mol) of chloretone are dried by boiling in benzene using a water separator and dissolved in 400 ml of dry $CH_2Cl_2$, 140 ml (2.0 mols) of phosgene are condensed into the resulting solution in the course of 1 hour at −20° C and 105 ml (1.5 mols) of pyridine in 70 ml of $CH_2Cl_2$ are added dropwise at −20° C. The mixture is stirred for a further 12 hours at 20° C, the solution is washed at 0° C with water, 2 N $H_2SO_4$ and water, dried ($Na_2SO_4$) and concentrated and 214 g (89%) of 2,2,2-trichloro-tert.-butoxycarbonyl chloride are obtained. Boiling point$_{12}$ = 77°- 81° C.

EXAMPLE 85

3.31 g (20 mmols) of L-valine methyl ester-hydrochloride and 5.05 g (21 mmols) of 2,2,2-trichloro-tert.-butoxycarbonyl chloride are reacted in the manner described in Example 6 a. Without recrystallization, 6.58 g (98%) of a white solid consisting of 2,2,2-tichloro-tert.-butoxycarbonyl-L-valine methyl ester are obtained. Melting point = 42 - 5° C. $[\alpha]_D^{25} = -8.13°$ (c = 1.0 in ethanol).

EXAMPLE 86

5.5 g (6.1 mmols) of lithium cobalt-phthalocyanine in 30 ml of methanol, 1.2 g (about 12 mmols) of phenol and 669 mg (2.0 mmols) of 2,2,2-trichloro-tert.-butoxycarbonyl-L-valine methyl ester are stirred for 10 minutes at 20° C. 30 ml of water and 2 g of citric acid are added to the deep green mixture at 0° C, the blue precipitate is centrifuged off and the residue is washed a further twice with water. The combined supernatant liquors are washed (3 times) with ether, rendered alkaline with sodium carbonate and extracted (4 times) with CH₂Cl₂. The combined CH₂Cl₂ extracts are dried over Na₂SO₄ and concentrated, whereupon 227 mg (87%) of L-valine methyl ester are obtained.

It will be appreciated that the instant specification and examples are set forth by way of illustration and not limitation, and that various modifications and changes may be made without departing from the spirit and scope of the present invention.

What is claimed is:

1. In the process for preparing an organic compound of the formula $$A' - X$$

in which
X is an amino group, a hydroxyl group or a carboxyl group, and
A' is the remainder of the molecule, from an organic compound of the formula $$A - X$$

in which
A is the remainder of the molecule which can undergo reaction to form A', by converting $A - X$ into a compound of the formula $$A - Z - COOR$$

in which
Z is —NH—, —O— or a direct C—C bond, and
R is a radical of the formula $$\begin{array}{cc} R^1 & R^3 \\ | & | \\ -C-Y-C-Hal \\ | & | \\ R^2 & R^4 \end{array}$$

in which
Y is a direct C-C single bond, the —CH=CH— group or an arylene group,
$R^1$ to $R^4$ each independently is hydrogen, halogen or an alkyl, aryl, aralkyl, alkoxycarbonyl, alkylaminocarbonyl, arylaminocarbonyl or cycloalkylaminocarbonyl radical, or
$R^1 + R^2$ and $R^3 + R^4$ each independently completes a 5- or 6-membered carbocyclic ring, or $R^1$ and $R^3$ conjointly with the grouping —C—Y—C— forms a carbocyclic ring with 5 or 6 carbon atoms, and
Hal is halogen,
thereby to protect X, then converting $A - Z - COOR$ into a compound of the formula $$A' - Z - COOR$$

and then treating the compound $A' - Z - COOR$ to restore the group X, the improvement which comprises effecting the treatment of the compound $A' - Z - COOR$ with an alkali metal compound of a complex of monovalent cobalt in which the complex of monovalent cobalt has the formula

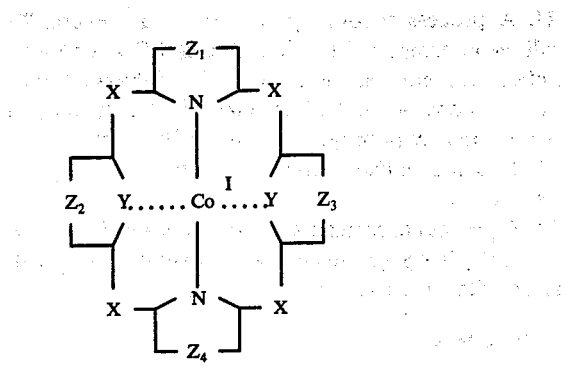

in which Y is nitrogen, oxygen or sulfur, $Z_1$, $Z_2$, $Z_3$ and $Z_4$ each independently is the grouping CH-CH, N-N, or CH-N, and together with Y or N forms a five-membered ring which is optionally substituted and optionally fused to an optionally substituted and optionally fused to an optionally substituted benzene nucleus, and X is a nitrogen atom or the grouping —CH₈, wherein R₈ denotes hydrogen, alkyl or aryl.

2. A process according to claim 1, in which Hal is chlorine, bromine or iodine.

3. A process according to claim 1 in which Y is a C-C direct bond or a p-phenylene group.

4. A process according to claim 1, in which $R^1$ to $R^4$ each independently is C₁-C₈ alkyl, phenyl, naphthyl, aralkyl with 7 to 10 carbon atoms, chlorine, bromine, iodine, alkoxycarbonyl with up to 4 carbon atoms in the alkyl part, alkylaminocarbonyl with up to 8 carbon atoms in the alkyl part, arylaminocarbonyl with 6 to 10 carbon atoms in the aryl part, or cycloalkylaminocarbonyl with 5 or 6 carbon atoms in the cycloalkyl part.

5. A process according to claim 4, in which $R^1$ to $R^4$ each independently is C₁-C₄ alkyl, phenyl, naphthyl, benzyl, phenethyl, metoxycarbonyl, ethoxycarbonyl, propylaminocarbonyl, butylaminocarbonyl, hexylaminocarbonyl, phenylaminocarbonyl, cyclopentylaminocarbonyl or cyclohexylaminocarbonyl.

6. A process according to claim 1, in which R is β-chloroethyl, β-bromoethyl, β,β-dichloroethyl, β,β-dibromoethyl, β,β,β-trichloroethyl, β-bromopropyl, β,β-dibromopropyl, β,β-dichloropropyl or γ-trichloromethylallyl.

7. A process according to claim 1, in which the compound A-X is a peptide, aminocarboxylic acid, penicillin S-oxide, cephalosporin, 6-aminopenicillanic acid, 7-aminocephalosporanic acid or aminodeacetoxycephalosporanic acid.

8. A process according to claim 1, in which the compound A-X is phenylglycine, p-hydroxyphenylglycine, phenylmalonic acid, thienylmalonic acid or mandelic acid.

9. A process according to claim 1, in which the compound A-X is phenylglycine or p-hydroxyphenylglycine and R is bromoethyl, chloroethyl, dibromoethyl, dichloroethyl, trichloroethyl, tribromoethyl or β,β-dibromopropyl.

10. A process according to claim 1, in which the compound A-X is a penicillin S-oxide and R is bromoethyl, dibromoethyl, dichloroethyl, trichloroethyl, β,β-dibromoethyl, α-tert.-butylaminocarbonyl-β-chloroethyl, α-cyclohexylaminocarbonyl-β-bromoethyl, α-cyclohexylaminocarbonyl-β-chloroethyl, α-cyclohexylaminocarbonyl-β-dichloroethyl or α-tert.-butylaminocarbonyl-β-dichloroethyl.

11. A process according to claim 1, in which the alkali metal compound is selected from lithium cobalt-(I)-phthalocyanine, sodium cobalt-(II)-phthalocyanine, potassium cobalt-(I)-phthalocyanine, sodium cobalt-(I)-meso-tetrophenylporphyrine and sodium bis-[2-(1'-imino-3'-isoindolenine)-5-amino-1,3,4-thiadiazolato]-cobaltate-(I).

12. A process according to claim 1, in which X is an amino or hydroxyl group and the compound A-X is first reacted with a halogenoformic acid ester of the formula Hal-CO-OR 13. A process according to claim 1, in which X is a carboxyl group and the compound A-X is first reacted with an alcohol of the formula

HO-R

14. A process according to claim 1, in which X is a carboxyl group in the form of a salt and the compound A-X is first reacted with a halide of the formula Hal-R 15. A process according to claim 1, in which X is a carboxyl group and the compound A-X is first reacted with a carbonyl compound of the formula $$R^5-CO-Y-\underset{\underset{R^4}{|}}{\overset{\overset{R^3}{|}}{C}}-Hal$$

in which
$R^5$ is hydrogen or alkyl, and with an isonitrile of the formula $R^7 - NC$, in which
$R^7$ is alkyl, phenyl or cycloalkyl.

16. A process according to claim 1, in which the group X is restored at a temperature from about −30° to +50° C.

17. A process according to claim 1, in which the molar ratio of protected group X to alkali metal compound is from about 1:4 to 1:2.

18. A process according to claim 1, in which the group X is restored in the presence of an inert organic solvent or diluent.

19. A process according to claim 1, in which the group X is restored in the presence of a reducing agent.

20. A process according to claim 1, in which the group X is restored in the presence of a phenol, the molar ratio of the phenol to the cobalt complex being about 4:1 to 1:1.

* * * * *